(12) United States Patent
Graham

(10) Patent No.: US 11,351,056 B2
(45) Date of Patent: Jun. 7, 2022

(54) LENS INDEXING ASSEMBLY

(71) Applicant: Ocular Instruments, Inc., Bellevue, WA (US)

(72) Inventor: Raymond D. Graham, Renton, WA (US)

(73) Assignee: OCULAR INSTRUMENTS, INC., Bellevue, WA (US)

( * ) Notice: Subject to any disclaimer, the term of this patent is extended or adjusted under 35 U.S.C. 154(b) by 201 days.

(21) Appl. No.: 16/711,259

(22) Filed: Dec. 11, 2019

(65) Prior Publication Data

US 2020/0188167 A1 Jun. 18, 2020

Related U.S. Application Data

(60) Provisional application No. 62/779,402, filed on Dec. 13, 2018.

(51) Int. Cl.
*A61F 9/00* (2006.01)
*G02C 7/04* (2006.01)

(52) U.S. Cl.
CPC ............ *A61F 9/0061* (2013.01); *G02C 7/049* (2013.01)

(58) Field of Classification Search
CPC ....... A61F 9/0061; G02C 7/049; G02B 7/023; A61B 3/117; A61B 3/125; A61B 3/10
See application file for complete search history.

(56) References Cited

U.S. PATENT DOCUMENTS

| 5,841,510 A | 11/1998 | Roggy |
| 6,183,085 B1 | 2/2001 | Roggy et al. |
| 7,419,262 B2 | 9/2008 | Whalen |

(Continued)

FOREIGN PATENT DOCUMENTS

| DE | 3831929 C2 | 9/1995 | |
| DE | 3831939 | * 9/1995 | ............. A61B 3/125 |

OTHER PUBLICATIONS

Extended European Search Report dated May 18, 2020, issued in European Patent Application No. 19215690.9, filed Dec. 12, 2019, 9 pages.

(Continued)

*Primary Examiner* — Darryl J Collins
*Assistant Examiner* — Matthew Y Lee
(74) *Attorney, Agent, or Firm* — Christensen O'Connor Johnson Kindness PLLC

(57) ABSTRACT

A lens indexing assembly is provided that includes a holding portion configured to support a rotating portion, wherein the holding portion has an outer surface configured for holding having a plurality of segments with recesses between segments and a bearing surface, a rotating portion configured for coupling with the holding portion, wherein the rotating portion is configured to rotate relative to the holding portion, and wherein the rotating portion has a bearing surface for rotating relative to the bearing surface of the holding portion, and wherein the rotating portion includes a plurality of tactile features on an outer surface, and an ophthalmic contact lens configured for coupling with the rotating portion, wherein the plurality of tactile features on the outer surface of the rotating portion are configured to provide tactile feedback corresponding to a plurality of angular (Continued)

positions of the ophthalmic contact lens relative to the holding portion.

15 Claims, 25 Drawing Sheets

(56) References Cited

U.S. PATENT DOCUMENTS

| | | | |
|---|---|---|---|
| 7,766,480 | B1 | 8/2010 | Graham et al. |
| 8,861,061 | B1 * | 10/2014 | Graham ................ A61B 3/117 |
| | | | 359/219.1 |
| 2010/0259669 | A1 | 10/2010 | Wood |
| 2015/0313464 | A1 * | 11/2015 | Graham ................ A61F 9/007 |
| | | | 351/246 |

OTHER PUBLICATIONS

Huber, C., "Three Ophthalmological Instruments: The Rotating Contact Glass Holder, the Cutying Forceps and the Diamond Cystotome," in J. Draeger and R. Winter (eds), vol. 18, "New Microsurgical Concepts II: Cornea, Posterior Segment, External Microsurgery," Series: "Developments in Ophthalmology," Karger, Basel, Switzerland, 1989, pp. 102-106.

Huber, C. et al., "The Rotating Contact Lens Holder," Klinische Monätsblatter für Augenheilkunde 193(7):78-79, Jul. 1988.

* cited by examiner

LENS INDEXING ASSEMBLY

CROSS-REFERENCE TO RELATED APPLICATION

This application claims the benefit of U.S. Provisional Application No. 62/779,402, filed Dec. 13, 2018, the disclosure of which is hereby incorporated by reference in its entirety.

BACKGROUND

A lens used in connection with gonioscopy, i.e., the viewing of the periphery of the anterior chamber of the eye, is known as a gonio lens or gonioscope. A gonio lens generally includes a contact lens element and one or more mirrors. The contact lens element has an optical axis and a concave contact surface that conforms to the anterior surface of the cornea of an eye. The contact lens element also has a viewing surface that is offset in an anterior direction from the contact surface. At least one mirror is arranged with its planar surface angled away from the optical axis of the contact lens element in an anterior direction. When the contact lens element is positioned on the eye, the mirrors reflect the light from the periphery of the anterior chamber of the eye into the direction of the observer, typically via a microscope for necessary magnification.

In one example, a gonio lens allows an observer to visually assess inflammation or structural defects in the trabecular meshwork and related adjacent structures in the eye. As another example, a gonio lens can be configured for viewing and treating an eye, such as an iridotomy goniolaser lens and a trabeculoplasty goniolaser lens (e.g., a Selective Laser Trabeculoplasty lens or SLT lens). The observer may assess the trabecular meshwork before, during, and after the treatment with laser energy to thereby assess the efficacy of the treatment. In other procedures, the gonio lens may be used in surgery.

Some lenses may include a plurality of mirrors, such as the Ocular Three Mirror Universal, manufactured by Ocular Instruments, Inc., of Bellevue, Wash., wherein the mirrors are circumferentially spaced respectively 120 degrees apart and are mounted at different angles of inclination. Each different mirror angle allows the user to inspect and evaluate different portions of the eye. Some lenses have a plurality of mirrors all having the same angle of inclination, such as the Ocular Posner Diagnostic and Surgical Gonio lens, also manufactured by Ocular Instruments, Inc., which can help reduce the need to rotate the mirror. As another example, a lens may include a single mirror, such as the Ocular Magna View Gonio, also manufactured by Ocular Instruments, Inc. As another example, a lens may include two mirrors, such as the Ahmed DVX direct view surgical gonio lens, also manufactured by Ocular Instruments, Inc., for an unreversed view, which is particularly helpful during surgical procedures.

The selection and position of the specific mirror to be used during an evaluation will depend upon the portion of the eye that needs to be evaluated. The selected mirror is generally positioned opposite the area to be evaluated. For example, if the 12 o'clock position of the peripheral retina needs to be evaluated and a mirrored lens is being utilized, an angled mirror can be positioned at the 6 o'clock position of the retina so as to view the affected area.

Whether a multiple mirror lens or a single mirror lens, it may be necessary to rotate the lens up to 360 degrees to examine the entire retina or other portions of the eye or to conduct a full treatment on the entire eye.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with an aspect of the present disclosure, a lens indexing assembly is provided. The lens indexing assembly, in an embodiment, comprises: a holding portion configured to support a rotating portion, wherein the holding portion has an outer surface configured for holding and a bearing surface; a rotating portion configured for coupling with the holding portion, wherein the rotating portion is configured to rotate relative to the holding portion, and wherein the rotating portion has a bearing surface for rotating relative to the bearing surface of the holding portion, the rotating portion having an interface for coupling to an ophthalmic contact lens; wherein the rotating portion includes a plurality of tactile features on an outer surface, and wherein the plurality of tactile features on the outer surface of the rotating portion are configured to provide tactile feedback corresponding to a plurality of angular positions of the ophthalmic contact lens relative to the holding portion.

In accordance with an aspect of the present disclosure, a lens indexing assembly is provided. The lens indexing assembly, in one embodiment, includes: a holding portion configured to support a rotating portion, wherein the holding portion has an outer surface configured for holding having a plurality of segments with recesses between segments and a bearing surface; a rotating portion configured for coupling with the holding portion, wherein the rotating portion is configured to rotate relative to the holding portion, and wherein the rotating portion has a bearing surface for rotating relative to the bearing surface of the holding portion, and wherein the rotating portion includes a plurality of tactile features on an outer surface; and an ophthalmic contact lens configured for coupling with the rotating portion, wherein the plurality of tactile features on the outer surface of the rotating portion are configured to provide tactile feedback corresponding to a plurality of angular positions of the ophthalmic contact lens relative to the holding portion.

In accordance with another embodiment of the present disclosure, a lens indexing assembly for coupling with an ophthalmic contact lens configured for rotating the ophthalmic contact lens by a user on the eye of a patient is provided. The lens indexing assembly, in an embodiment, includes: a holding portion configured to support a rotating portion, wherein the holding portion has an outer surface configured for holding and a bearing surface having a plurality of segments with recesses between segments; and a rotating portion configured for coupling with the holding portion, wherein the rotating portion is configured to rotate relative to the holding portion, and wherein the rotating portion has a bearing surface for rotating relative to the bearing surface of the holding portion, and wherein the rotating portion includes a plurality of tactile features on an outer surface, and wherein the plurality of tactile features on the outer surface of the rotating portion are configured to provide tactile feedback corresponding to a plurality of angular positions of the ophthalmic contact lens relative to the holding portion.

In accordance with another embodiment of the present disclosure, a method of using a lens indexing assembly is provided. The method includes: obtaining portions of a lens indexing assembly including: a holding portion configured to support a rotating portion, wherein the holding portion has an outer surface configured for holding and a bearing surface having a plurality of segments with recesses between segments, wherein at least two of the segments of the bearing surface of the rotating portion are flexible segments; a rotating portion configured for coupling with the holding portion, wherein the rotating portion is configured to rotate relative to the holding portion, and wherein the rotating portion has a bearing surface for rotating relative to the bearing surface of the holding portion, and wherein the rotating portion includes a plurality of tactile features on an outer surface; and an ophthalmic contact lens configured to be coupled to the rotating portion; attaching the holding portion and the rotating portion by depressing the flexible segments of the bearing surface of the rotating portion; coupling the holding portion and the rotating portion; coupling the lens and the rotating portion; placing the lens in contact with a patient's eye; and holding the holding portion of the lens indexing assembly with first and second fingers on a single hand of a user, and rotating the rotating portion from a first angular position to a second angular position using a third finger on the same hand of the user.

In any of the embodiments described herein, the plurality of tactile features on the outer surface of the rotating portion may be indentations on surface of the rotating portion.

In any of the embodiments described herein, the plurality of tactile features on the outer surface of the rotating portion may be configured to receive a user's fingertip.

In any of the embodiments described herein, each edge of each of the plurality of tactile features on the outer surface of the rotating portion may be used as a lever for the user's fingertip to rotate the rotating portion relative to the holding portion.

In any of the embodiments described herein, the holding portion may include at least one tactile feature on the outer surface of the holding portion.

In any of the embodiments described herein, each one of the plurality of tactile features on the outer surface of the rotating portion may be configured to be alignable with the at least one tactile feature on the outer surface of the holding portion.

In any of the embodiments described herein, the at least one tactile feature on the outer surface of the holding portion may be configured to align with the plurality of tactile features on the outer surface of the rotating portion to provide tactile feedback corresponding to a plurality of angular positions of the ophthalmic contact lens.

In any of the embodiments described herein, the at least one tactile feature on the outer surface of the holding portion may be configured to align with the plurality of tactile features on the outer surface of the rotating portion to provide tactile feedback corresponding to at least one indexing position.

In any of the embodiments described herein, the holding portion may include a plurality of tactile features on the outer surface of the holding portion.

In any of the embodiments described herein, the plurality of tactile features on the outer surface of holding portion may be the same as or different than in number as the plurality of tactile features on the outer surface of the rotating portion.

In any of the embodiments described herein, a resistance to rotation of the rotating portion may be caused by frictional contact between the holding portion and the rotating portion.

In any of the embodiments described herein, the resistance to rotation may be substantially constant at all of the plurality of angular positions of the ophthalmic contact lens.

In any of the embodiments described herein, the rotating portion may include a ring bezel to releasable receive the ophthalmic contact lens.

In any of the embodiments described herein, the rotating portion may be releasably coupled to the holding portion.

In any of the embodiments described herein, at least two of the segments of the bearing surface of the rotating portion may be flexible segments.

In any of the embodiments described herein, the flexible segments may be depressible to coupled and decouple the rotating portion and the holding portion.

In any of the embodiments described herein, the plurality of tactile features on the outer surface of the rotating portion may be indentations, each indentation having at least two edges used for leverage in rotating.

In any of the embodiments described herein, the ophthalmic contact lens may be a gonio lens.

In any of the embodiments described herein, the ophthalmic contact lens may include at least one mirror placed at an angle relative to the optical axis of the eye.

In any of the embodiments described herein, a method may further include using the plurality of tactile features on the outer surface of the rotating portion to receive tactile feedback corresponding to a plurality of angular positions of the ophthalmic contact lens relative to the holding portion.

In any of the embodiments described herein, a method may further include using the third finger on the same hand of the user, rotating the rotating portion from the second angular position to a third angular position.

In any of the embodiments described herein, the first and second fingers may be the thumb and index or middle finger.

In any of the embodiments described herein, the third finger may be the middle or index finger.

In any of the embodiments described herein, the lens indexing assembly includes an ophthalmic contact lens configured for coupling with the rotating portion.

In any of the embodiments described herein, one of the outer surface of the holding portion or the bearing surface has a plurality of segments with recesses between segments; wherein the segments are depressible to coupled and decouple the rotating portion and the holding portion.

In any of the embodiments described herein, each indentation has a U-shape.

In any of the embodiments described herein, a resistance to rotation of the rotating portion is provided by frictional contact between the holding portion and the rotating portion, the resistance to rotation being substantially constant at all of the plurality of angular positions of the ophthalmic contact lens.

In any of the embodiments described herein, the plurality of tactile features on the outer surface of the rotating portion are U-shaped channels, each U-shaped channel having at least two outer edges used for rotating the rotating portion with respect to the holding portion, each U-shaped channel having side walls that are substantially parallel to each other and oriented orthogonally to a bottom wall of the U-shaped channel.

In accordance with another aspect of the present disclosure, a method of using a lens indexing assembly is provided. The method includes, in various embodiments, providing a lens indexing assembly according to any of embodiments described herein, the lens indexing assembly further comprising an ophthalmic contact lens configured for coupling with the rotating portion; placing the lens in contact with a patient's eye; and holding the holding portion of the lens indexing assembly with first and second fingers on a single hand of a user, and rotating the rotating portion from a first angular position to a second angular position using a third finger on the same hand of the user.

DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein.

DETAILED DESCRIPTION

Figure 1:
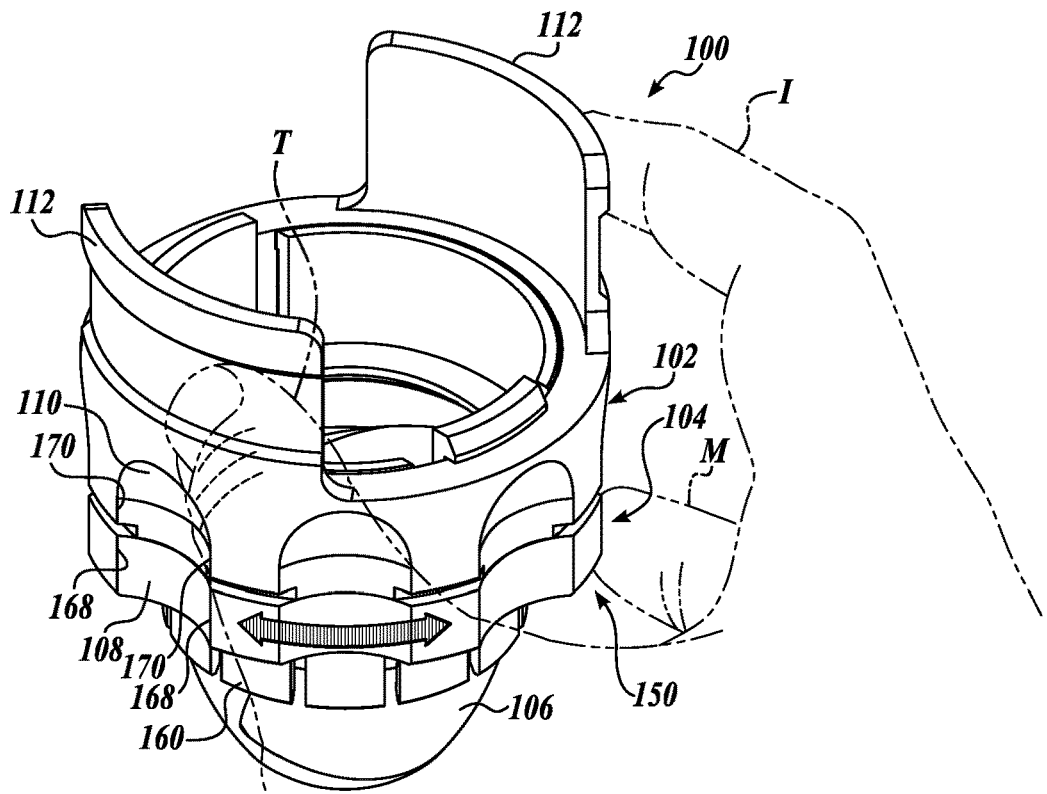
FIG. 1 is a diagrammatical illustration of a lens assembly in accordance with one embodiment of the present disclosure.

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Accordingly, the following descriptions and illustrations herein should be considered illustrative in nature, and thus, not limiting the scope of the disclosed subject matter.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Language such as, but not limited to, "top surface", "bottom surface", "side edge", "vertical", "horizontal", and "lateral" in the present disclosure is meant to provide orientation for the reader with reference to the drawings and is not intended to be the required orientation of the components or to impart orientation limitations into the claims.

Embodiments of the present disclosure are generally directed to indexing lens assemblies, and methods of indexing a rotating portion with lens relative to a holding portion, such as a contact lens or a gonio lens assembly used in optometry and ophthalmology. As used herein "indexing" refers to achieving precise rotation of a lens assembly in uniform increments. Each incremental rotated position is sometimes referred to as an "indexing position". In an embodiment, an indexing position is achieved via tactile feedback in the form of surface contour alignment of a tactile feature of the rotating portion and lens with a tactile feature of the holding portion supporting the rotating portion. In other embodiments, an indexing position may be achieved by tactile feedback in the form of a user understanding relative positioning of adjacent fingers on the user's hand.

In some embodiments of the present disclosure, the rotating portion and/or the holding portion of the indexing lens assembly can each include one or more tactile features on the exterior periphery to achieve an indexing position when the tactile features on the rotating portion become aligned with the tactile features on the holding portion. The indexing positions correspond to predetermined angular positions of the ophthalmic lens relative to a central axis through the indexing lens assembly. In some embodiments of the present disclosure, achieving alignment does not rely on sensing increased resistance to rotation or even visually sighting the alignment. Achieving an indexing position in accordance with some embodiments of the present disclosure is sensed through tactile feedback by the fingertips sensing when a tactile feature is in alignment with another tactile feature.

In some embodiments of the present disclosure, resistance to rotation is the normal resistance that is inherent when a plain bearing surface of the rotating portion is in contact with a second plain bearing surface of the holding portion when the lens indexing assembly in in contact with an eye. In embodiments of the present disclosure, the resistance to rotation is substantially constant at all angular positions of the ophthalmic contact lens, even at the indexing positions and from one indexing position toward another indexing position.

Referring to FIGS. 1-6, one embodiment of a lens indexing assembly 100 in accordance with the present disclosure can be seen. The lens indexing assembly 100 in the illustrated embodiment includes a holding portion 102, a rotating portion 104 configured to rotate relative to the holding portion 102, and a lens 106 attached with the rotating portion 104 such that the rotating portion 104 and lens 106 rotate together as a unit. The rotating portion 104 rotates relative the holding portion 102 (as indicated by the arrow in FIG. 1) to achieve indexing positions that help the user orient the positioning of the rotating portion 104 and lens 106 relative to the holding portion 102. As described further below, the indexing positions of the illustrated embodiment are achieved when tactile features 108 on the rotating portion 104 are in alignment with tactile features 110 on the holding portion 102. In other embodiment of the present disclosure, the indexing positions are achieved when tactile features on the rotating portion are rotated by a finger on the hand of a user in reference to other fingers on the hand of a user, as described in greater detail below.

Holding Portion

Figure 3:
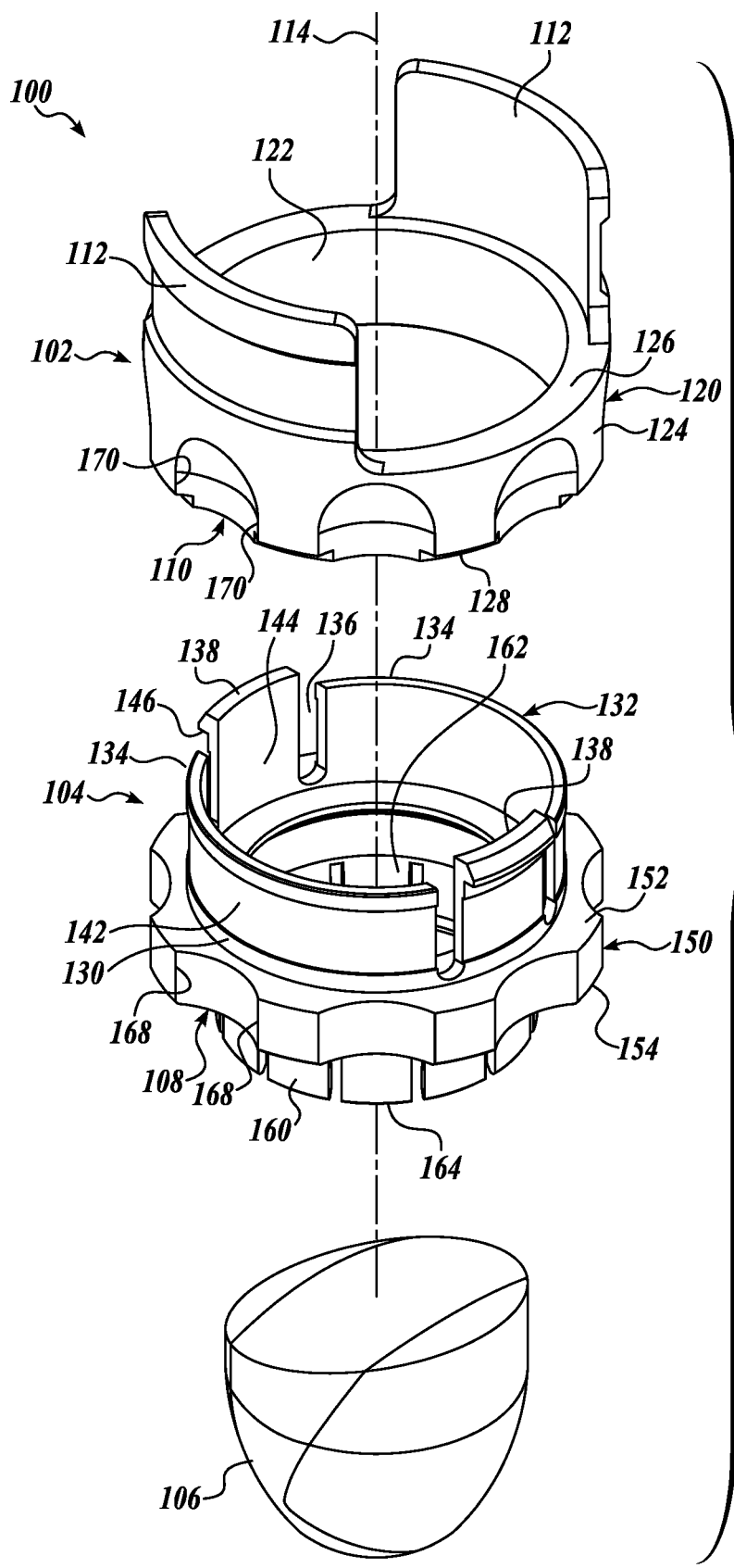
FIG. 3 is a diagrammatical illustration of the lens assembly of FIG. 1 in exploded format to show the major parts.

Referring to the exploded view in FIG. 3, the holding portion 102 is generally comprised of an annular body 120 defining inner and outer surfaces 122 and 124 and top 126 and bottom 128 axial surfaces. The annular body 120 defines an inner bore having a central axis 114 to permit viewing through the holding portion 102 to the lens 106 when the lens indexing assembly 100 is assembled. In use, the central axis 114 generally aligns with the optical axis of the eye.

Extending from the top axial surface 126 of the body 120 in the illustrated embodiment, the holding portion 102 includes holding tabs 112, which are configured for allowing a user to hold the holding portion 102 with a thumb T and index finger I (see FIG. 1). In that regard, the holding portion 102 and the holding tabs 112 are sized, designed, and configured for user comfort. The spacing between the holding tabs 112, allows for adequate light to enter the inner bore of the holding portion 102 to permit illumination through the holding portion 102 to the lens 106 when the lens indexing assembly 100 is assembled. In other embodiments, however, the holding portion 102 may include a different holding configuration, for example, a continuous holding portion instead of holding tabs 112.

As described above, the rotation portion 104 of the lens indexing assembly 100 is configured for rotational movement relative to the holding portion 102. In the illustrated embodiment, the inner surface 122 of the holding portion 102 is a smooth surface having an even and regular surface substantially free from perceptible projections or indentations, and functions as a plain bearing surface when mated to the rotating portion 104.

In the illustrated embodiment, the outer surface 124 of the holding portion 102 includes a plurality of tactile features 110. In the illustrated embodiment, the tactile features 110 are spaced evenly or uniformly around the outer surface 124 of the holding portion 102. However, other non-uniform spacing of the tactile features 110 is within the scope of the present disclosure.

The outer surface 124 of the holding portion 102 can be considered to have an outer radius from the central axis 114 of the holding portion 102 in places where there is an absence of the tactile features 110. The tactile features 110 extend to a radius that can be different from the outer radius of the outer surface 124. In some embodiments, each tactile feature 110 on the outer surface 124 can have the same arc length along the outer surface 124, and each tactile feature 110 can be spaced apart from the adjacent tactile features by a similar arc length. The arc length of the tactile features 110 extend from side edge 170 to side edge 170.

The space on the outer surface 124 between the tactile features 110 can be considered to have the outer radius of the outer surface 124. In the illustrated embodiment, the tactile features 110 extend axially at least to the lower outer edge between the outer surface 124 and a bottom axial surface 128 of the holding portion 102, but in this embodiment, do not need to extend axially to the upper edge between the outer surface 124 and a top axial surface 126 of the holding portion 102. Placing the tactile features 110 at least to the lower outer edge can help facilitate alignment with the tactile features 108 of the rotating portion 104.

In the illustrated embodiment, the tactile features 110 are indentations in the outer surface 124 of the holding portion 102. Therefore, the tactile features 110 extend to a radius less than the outer radius of the outer surface 124. In some embodiments, the tactile features can be protrusions instead of indentations, for example, with the protrusions extending to a radius greater than the outer radius of the outer surface 124. In some embodiments, the tactile features can be any surface contours, such as indentations or protrusions that differ with respect to radius from the outer radius of the outer surface 124.

In the illustrated embodiment, the tactile features 110 comprise indentations defined to receive the fingertip of a user. Such tactile features can be referred to as "fingertip grooves" because they are configured to accommodate the size and shape of an average finger. In the illustrated embodiment, the tactile features 110 are rounded indentations extending between side edges 170 having a partial cylindrical shape and a partial spherical shape adjoined together. In some embodiments, the tactile features 110 can be indentations having other shapes. For example, in some embodiments, the tactile features 110 can only comprise partial cylindrical shape and a partial spherical shape. In some embodiments, the tactile features 110 do not require roundness, but can be square or rectangular shapes. In some embodiments, the tactile features 110 can be V-shaped indentations.

As described in greater detail below, the lower axial surface 128 of the holding portion 102 functions as an axial plain bearing surface. As described in detail below, the rotating portion 104 of the indexing lens assembly 100 is connected to the holding portion 102 such that an upper axial surface 152 of the rotating portion 104 is located adjacent the bottom axial surface 128 of the holding portion 102.

Rotating Portion

Referring to the rotating portion 104 in FIG. 3, the rotating portion 104 is generally comprised of an annular body 130 defining an inner bore having a central axis 114 to permit viewing through the lens 106 when the lens indexing assembly 100 is assembled. As seen in FIG. 3, the central axis 114 of the rotating portion 104 is co-axial with the central axis 114 of the holding portion 102 when the lens indexing assembly 100 is assembly.

The rotating portion 104 includes a first (top) section defining a coupling section 132 configured for coupling with the holding portion 102, a second (middle) section defining a tactile section 150 including tactile features 108 configured for aligning with the tactile features 110 on the holding portion 102, and a third (bottom) section defining a lens holding section 160 configured for holding a lens 106.

The coupling section 132 of the rotation portion 104 is a cylindrical section including a plurality of partial cylindrical segments 134 and 138 extending from the annular body 130, all of similar inner and outer radiuses in a circular arrangement, configured for coupling the rotation portion 104 with the holding portion 102. First and second cylindrical segments 134 each have an outer surface 142 which functions as a radial plain bearing surface that is configured to rotate against the inner plain bearing surface 122 of the holding portion 102 when the rotation portion 104 and the holding portion 102 are coupled together. The outer surface 142 is of a slightly smaller radius than the inner surface 122 of the holding portion 102 to allow for coupling of the two portions 102 and 104.

The first and second cylindrical segments 134 may be considered rigid or semi-rigid, while the third and fourth cylindrical segments 138 may be considered to be more flexible than the first and second segments 134. In the illustrated embodiment, the first and second segments 134 make up a majority of the circumference in order to be rigid, while the third and fourth segments 138 make up a smaller portion of the total circumference, which allows the third and fourth segments 138 to flex relative to the first and second segments 134. In some embodiments, the rigid and flexible segments may be made from the same material. In other embodiments, the rigid and flexible segments may be made from different materials to provide for a difference in flexibility.

Figure 4:
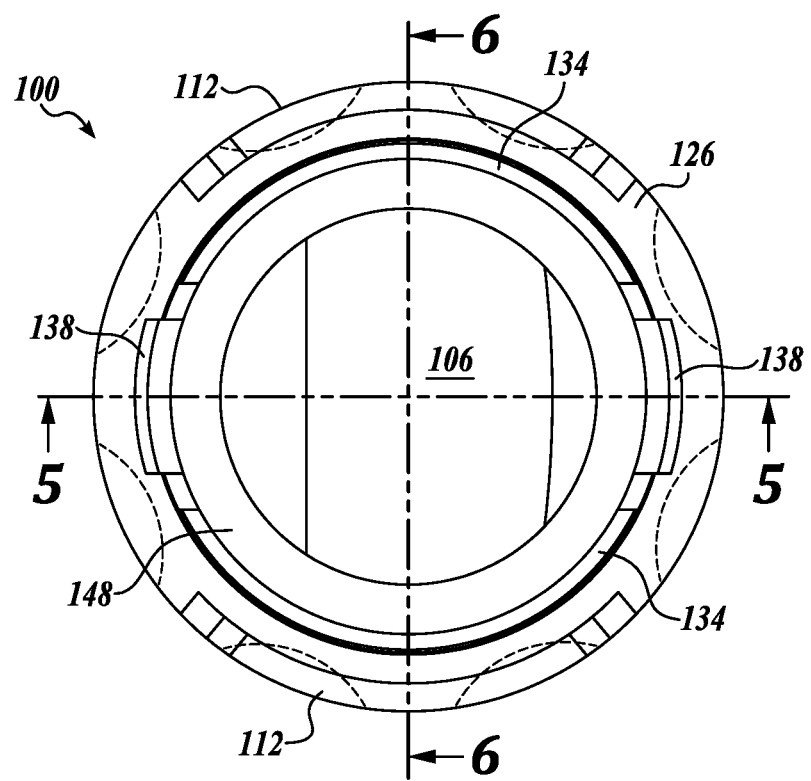
FIG. 4 is top view through the lens assembly of FIG. 1.

As can be seen in FIG. 4, the first and second segments 134 are larger than the third and fourth segments 138. Recesses 136 between adjacent segments allow the third and fourth segments 138 to flex relative to the first and second segments 134.

Figure 5:
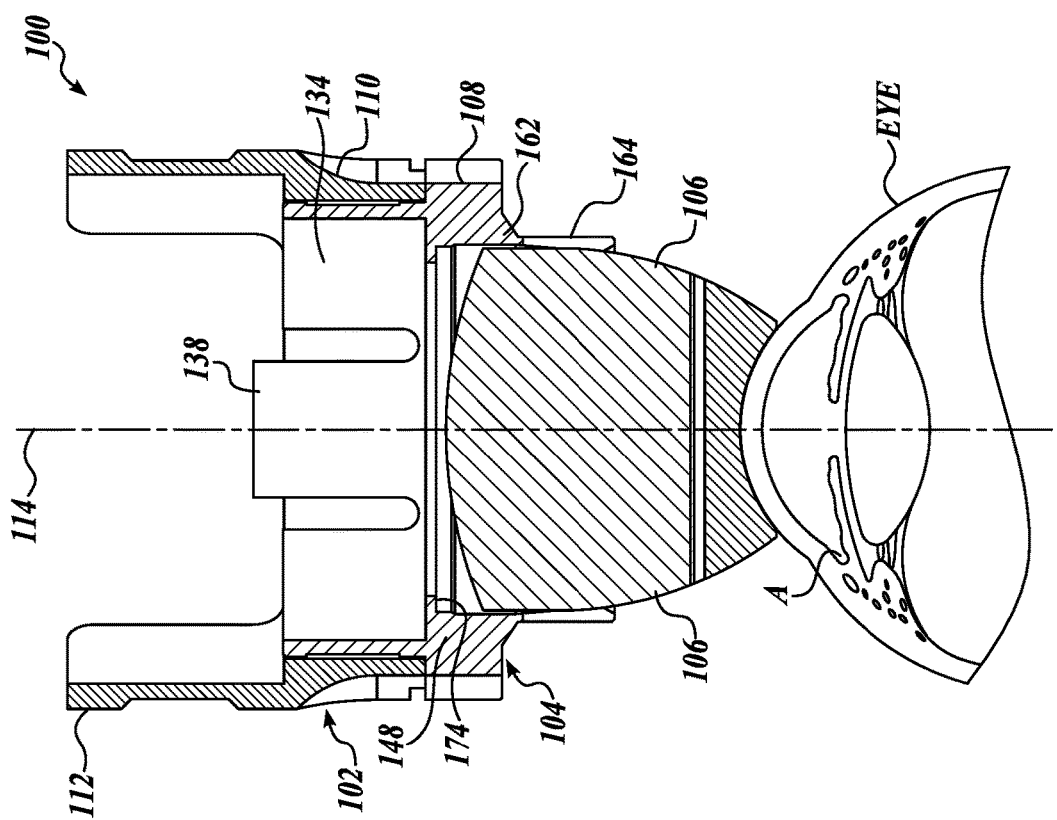
FIGS. 5 and 6 are cross-sectional side view of the lens assembly of FIG. 1 shown in contact with the eye of a patient.

The flexible segments 138 may comprise a portion of the radial plain bearing surface 142. However, a function of the segments 138 is to keep the rotation portion 104 axially aligned with the holding portion 102 when two are coupled together. In the illustrated embodiment, each flexible segment 138 includes an axial shank 144 and a radial barb 146. The axial shank 144 is slightly greater in the axial dimension than the axial dimension of the holding portion 102. This height difference allows the radial barb 146 to clear the holding portion 102 and come to rest on the axial upper surface 126 as seen in FIGS. 1 and 5. Referring to FIG. 3 again, the radial barb 146 extends out from the axial shank 144. The radial barb 146 has an underside surface that makes contact with the axial upper surface 126 of the holding portion 102 to keep the rotating portion 104 axially aligned within the holding portion 102. As seen in FIG. 3, the axial upper surface 126 of the holding portion extends around the entirety of the annular wall 120 of the holding portion 102, allowing for 360 degree rotation of the rotation portion 104 relative to the holding portion 102.

Further, the flexible cylindrical segments 138 also render the rotating portion 104 separable from the holding portion 102. First, to attach the rotating portion 104 to the holding portion 102, the flexible segments 138 can be depressed radially so that the radial barbs 146 clear the inner radius of the holding portion 102, and the rotating portion 104 is slipped into the holding portion 102 such that the plain bearing surface 142 of the rotating portion 104 is mated against the inner plain bearing surface 122 of the holding portion 102. When coupled, a radial surface of the radial barbs 104 is in close proximity with the upper surface 126 of the holding portion 102. To release, the radial barbs 104 can be depressed radially and the rotating portion 104 can be decoupled from the holding portion 102.

When the holding portion 102 and the rotation portion 104 are coupled, the tactile features 108 of the tactile section 150 of the rotation portion 104 are positioned adjacent the tactile features 110 on the holding portion 102 and configured for alignment.

In the illustrated embodiment, the rotating portion 104 and holding portion 102 are separable from one another for cleaning and sterilization, for example, for ophthalmic examination or surgical procedures. However, it should be appreciated that the rotating portion 104 need not be removable from the holding portion 102. In that regard, the rotating portion 104 may be configured without flexible cylindrical segments 138. In such configuration, the rotating portion 104 would be permanently rotatably coupled to the holding portion 102.

Other coupling configurations between the holding portion 102 and the rotating portion 104 are also within the scope of the present disclosure. For example, in one non-limiting example, the rotating portion 104 may optionally include a projection and groove system to maintain the rotating portion 104 on the holding portion 102, as described in U.S. Pat. No. 6,183,085, issued to Roggy et al, the disclosure of which is hereby expressly incorporated by reference in its entirety herein.

The rotating portion 104 further includes a tactile section 150 including tactile features 108 configured for aligning with the tactile features 110 on the holding portion 102. When the plain bearing surface 142 of the rotating portion 104 is aligned with the plain bearing surface 122 the holding portion 102, the tactile features 108 of the rotating portion 104 are adjacent and can be aligned with the tactile features 110 on the holding portion 102 as the rotating portion 104 rotates relative to the holding portion 102. (See, for example, alignment of tactile features 108 and 110 in FIG. 1.)

Figure 2:
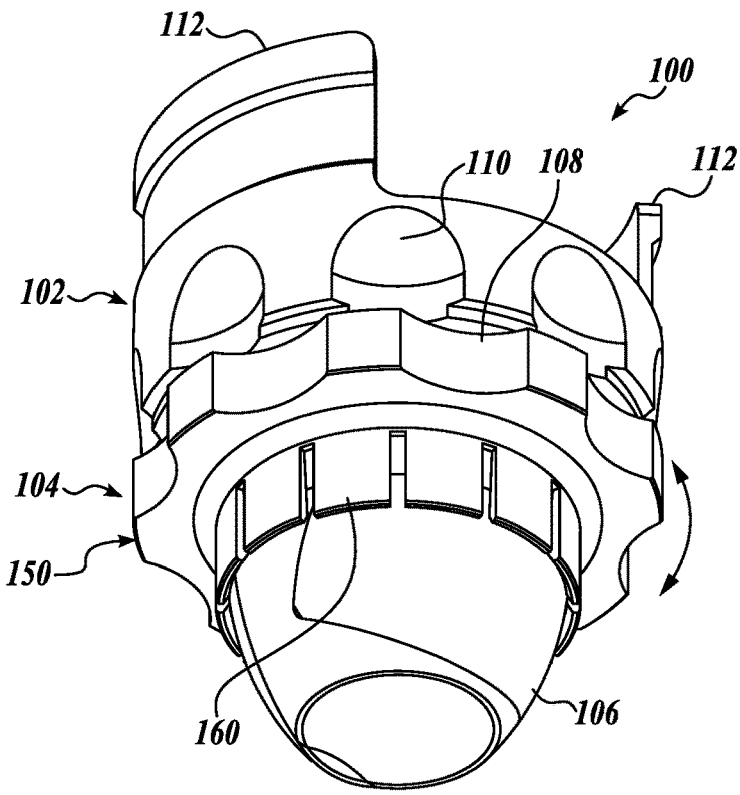
FIG. 2 is a diagrammatical illustration of the lens assembly of FIG. 1

The tactile section 150 of the rotating portion 104 extends radially from the annular body 130 of the rotating portion 104. The tactile section 150 is the middle section of the rotating portion 104, between the coupling section 132 and the lens holding section 160. The tactile section 150 comprises part of the exterior periphery of the lens indexing assembly 100 as seen in FIGS. 1 and 2, with the outer radius of the outer surface of the tactile section 150 being the same as the outer radius of the holding portion 102.

The tactile features 108 are located around the exterior periphery of the tactile section 150. The tactile features 108 extend axially in the tactile section 150 at least to the upper axial surface 152 of the tactile section 150 of the rotating portion 104. The rotating portion 104 is connected to the holding portion 102 such that the upper axial surface 152 of the tactile section 150 is located adjacent the bottom axial surface 128 of the holding portion 102. This relationship between the tactile section 150 of the rotating portion 104 and the bottom axial surface 128 of the holding portion 102 places the tactile features 108 of the rotating portion 104 adjacent to the tactile features 110 of the holding portion 102. In this manner, the tactile features 108 on the tactile section 150 of the rotating portion 104 can be aligned with the tactile features 110 on the holding portion 102.

When the holding portion 102 is coupled to the rotating portion 104, the upper axial surface 152 of the tactile section 150 of the rotating portion 104 is adjacent the bottom axial surface 128 of the holding portion 102 and acts as a plain bearing surface. Therefore, the holding portion 102 is coupled to the rotating portion 104 by being held between the radial barbs 138 of the coupling portion 132 of the rotating portion 104 and the upper axial surface 152 of the tactile section 150 of the rotating portion 104. The external bearing surface 142 of the coupling section 132 of the rotating portion 104 is in a bearing relationship with the interior bearing surface 122 of the holding portion 104. See FIGS. 5 and 6.

The upper axial surface 152 of the tactile section 150 of the rotating portion 104 supports the partial cylindrical segments 134 and 138 of the coupling section 132 of the rotating portion 104. The inner radius of the tactile section 150 can coincide with the inner radius of the coupling section 132. The tactile section 150 and the coupling section 132 can be formed as a single unit or can be separable.

Like the outer surface 124 of holding portion 102, the outer surface 154 of the rotating portion 104 can be considered to have an outer radius from the central axis 114 of the rotating portion 104 in places where there is an absence of the tactile features 108. The tactile features 108 extend to a radius that can be different from the outer radius of the outer surface 154. In some embodiments, each tactile feature 108 on the outer surface 154 can have the same arc length along the outer surface 154, and each tactile feature 108 can be spaced apart from the adjacent tactile features by a similar arc length. The space on the outer surface 154 between the tactile features 108 can be considered to have the outer radius of the outer surface 154. Further, the tactile features 108 extend axially at least to the upper outer edge between the outer surface 154 and the upper axial surface 152 of the rotating portion 104, but, do not need to extend axially to the upper edge. Placing the tactile features 108 at least to the lower upper edge will facilitate alignment with the tactile features 110 of the holding portion 102.

In the illustrated embodiment, the tactile features 108 are indentations in the outer surface 154 of the rotating portion 104. Therefore, the tactile features 108 extend to a radius less than the outer radius of the outer surface 154. In other embodiments, the tactile features may be protrusions instead of indentations, for example, extending to a radius greater than the outer radius of the outer surface 154. In some embodiments, tactile features 108 can be any surface contours, such as indentations or protrusions that differ with respect to radius from the outer radius of the outer surface 154.

In the illustrated embodiment, the tactile features 108 comprise indentations defined to receive the fingertip of a user. Such tactile features can be referred to as "fingertip grooves" because they are configured to accommodate the size and shape of an average fingertip. In the illustrated embodiment, the tactile features 108 are rounded indentations having a partial cylindrical shape. In some embodiments, the tactile features 108 can be indentations having other shapes. For example, in some embodiments, the tactile features 108 can only comprise partial cylindrical shape and a partial spherical shape. In some embodiments, the tactile features 108 do not require roundness, but can be square or rectangular shapes. In some embodiments, the tactile features 108 can be V-shaped indentations.

The rotating portion 104 further includes a holding section 160 configured to hold the lens 106. Suitable lenses for use in the lens indexing assembly 100 of the present disclosure include a variety of lenses. In an embodiment, the lens 106 is a lens used in ophthalmology, including, but not limited to, a gonio lens. A gonio lens is especially suited to be used in the lens indexing assembly 100 because a gonio lens includes at least one mirror to reflect light depending on the direction the mirror is pointed. Thus, the lens indexing assembly 100 is particularly suited as a gonioscope to view the periphery of the anterior chamber of the eye.

In the illustrated embodiment, the lens 106 is an unreversed prism gonioscopy lens assembly designed to view the periphery of the anterior chamber angle A of the eye. In that regard, the lens assembly 100 of the illustrated embodiment is a two-mirrored lens for an unreversed view.

Referring to FIG. 2, the holding section 160 is configured to hold the lens 106 with an interference fit such that the lens 106 can be held in place to rotate with the rotating portion 104 and such that the lens 106 may be removable from the rotating portion 104 for cleaning and sterilization.

Figure 6:
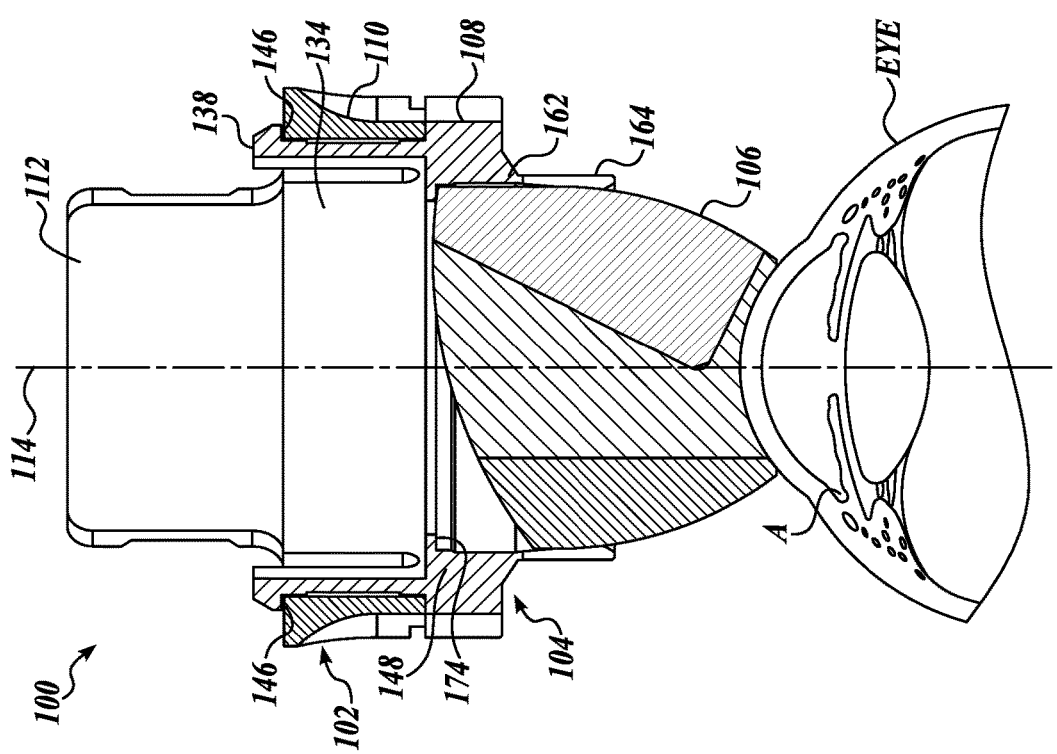
Figure 7:
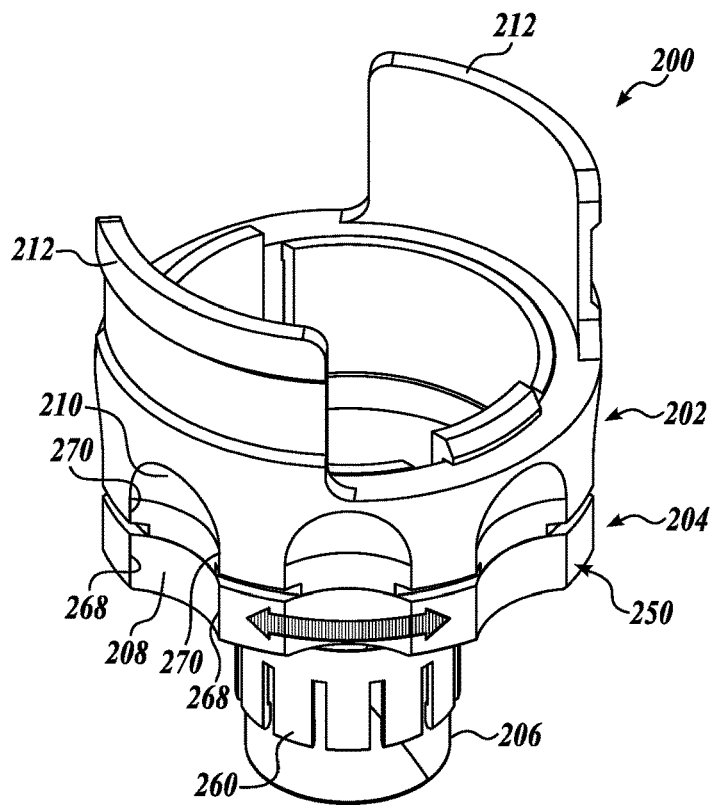
FIGS. 7-12 are diagrammatical illustrations of a lens assembly, similar to the diagrammatical illustrations in FIGS. 1-6, but in accordance with another embodiment of the present disclosure.
Figure 8:
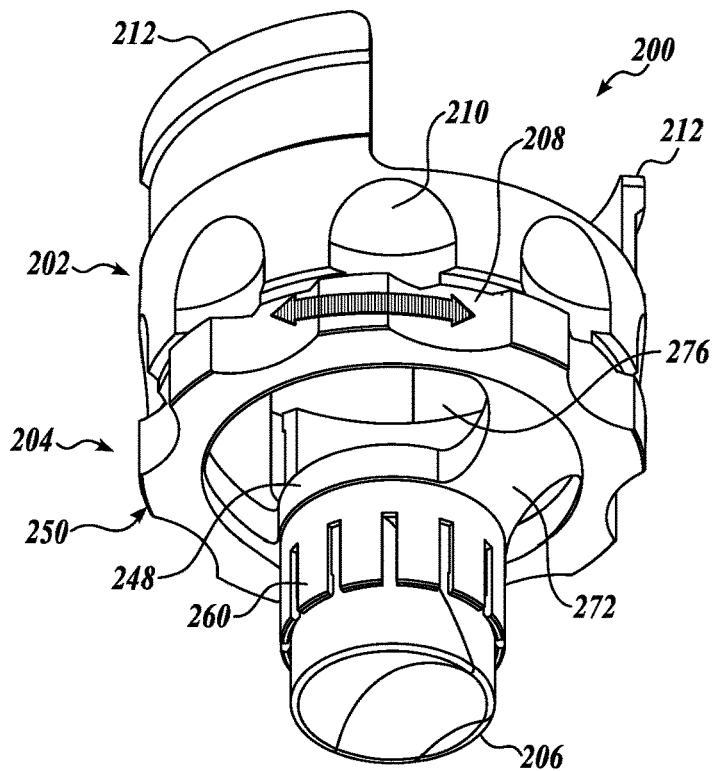

In the illustrated embodiment, the holding section 160 includes a bezel ring 162 comprising a plurality of crenulations or segregated teeth 164 extending from the inner circumference of the rotating portion 104 (see FIGS. 5 and 6). The teeth 164 flex when the lens 106 is inserted such that the lens 106 can be held by a friction fit within the crenulations. The lens 106 may be replaceable. Alternatively, the lens 106 can be held in the bezel ring 162 through an adhesive. As seen in FIGS. 5 and 6, an inwardly extending stopping protrusion 174 keeps the lens 106 from being inserted past the holding section 160.

Lens

In an embodiment, the lens 106 is an unhoused lens. As can be seen in FIG. 2, the lens 106 protrudes from the rotating portion 104 to enable direct contact of the lens 106 with the eye of a patient. An unhoused lens 106 allows for more light to enter the lens from the side to enhance the viewing capabilities of the lens, as compared to light inhibited by a housing for receiving a lens.

In one embodiment, the lens 106 has a frustoconical shape. One non-limiting example of a suitable lens is shown and described in U.S. Pat. No. 7,766,480, issued to Graham et al., the disclosure of which is hereby expressly incorporated by reference. Another nonlimiting example of a suitable lens is shown and described in U.S. Application Publication No. 2015/0313465 to Graham et al., the disclosure of which is hereby expressly incorporated by reference.

In one embodiment, the lens may be an Ocular Magna View Gonio, manufactured by Ocular Instruments, Inc. Other non-limiting examples of lenses may include multiple mirror arrangements, such as the Ocular Three Mirror Universal, wherein the mirrors are circumferentially spaced respectively 120° apart and are mounted at different angles of inclination, for example, 59°, 67°, and 73° relative to the vertical, and the Ocular Posner Diagnostic and Surgical Gonioprism with a plurality of mirrors all having the same angle of inclination, both also manufactured by Ocular Instruments, Inc.

Figure 9:
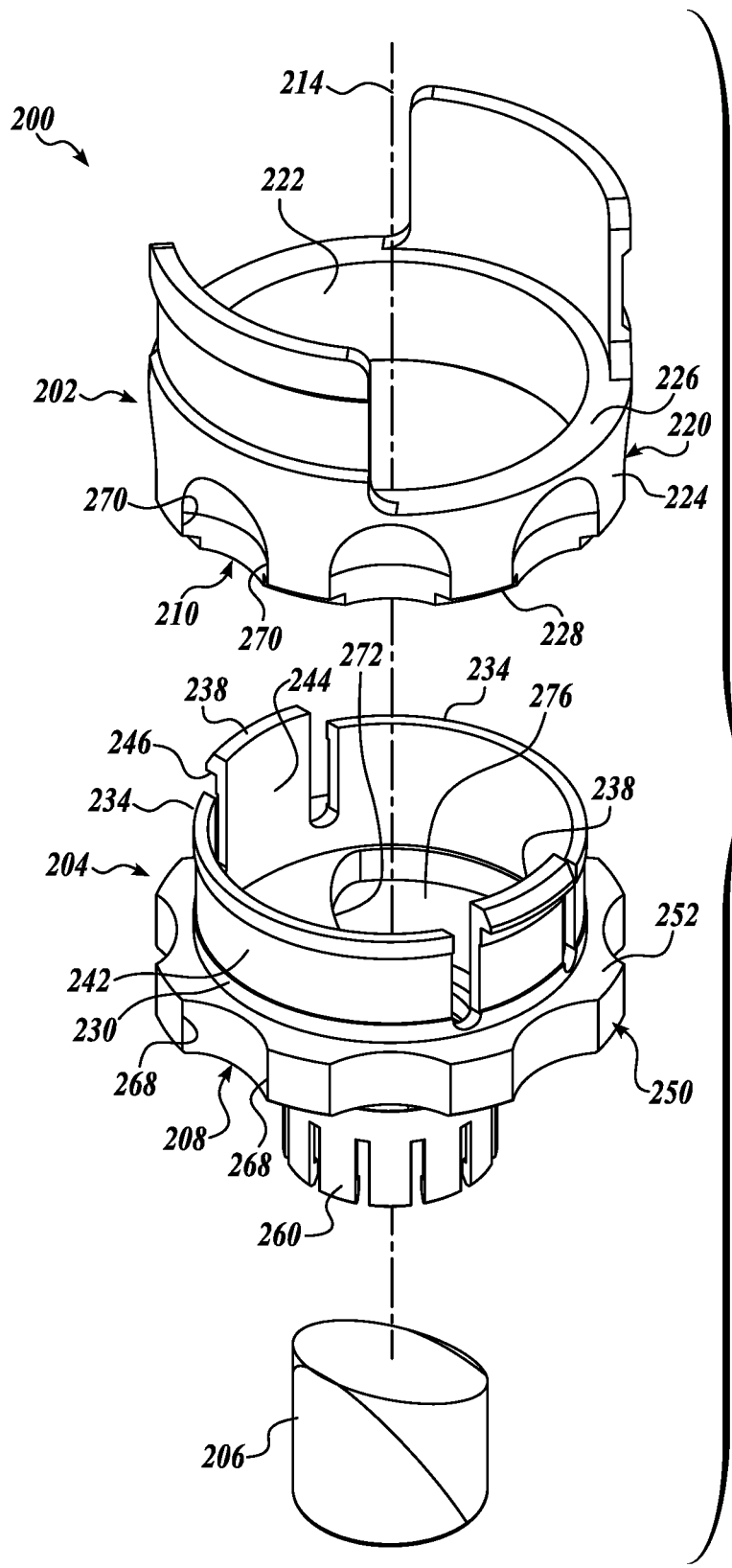
Figure 10:
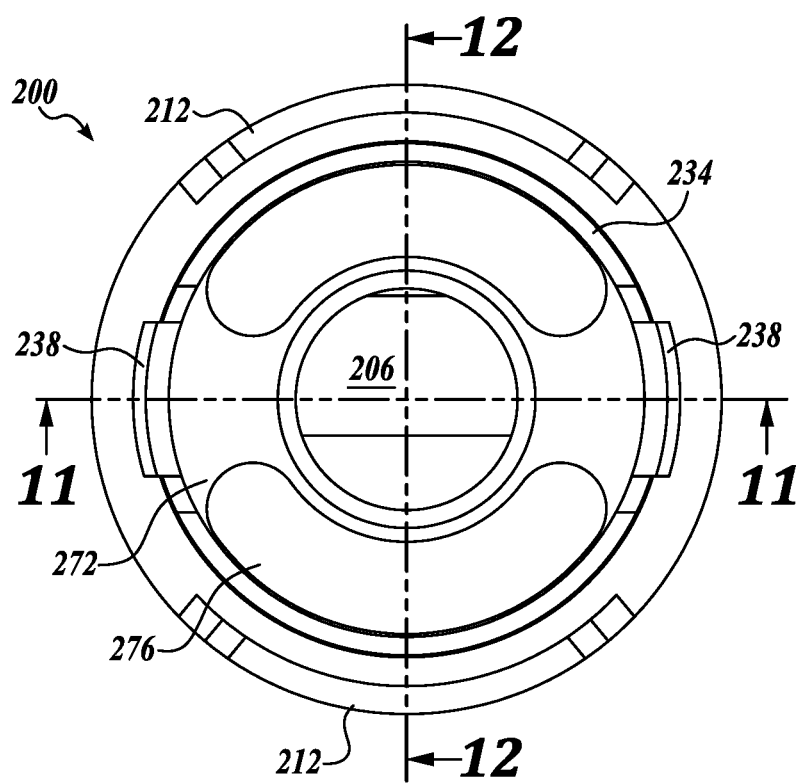
Figure 11:
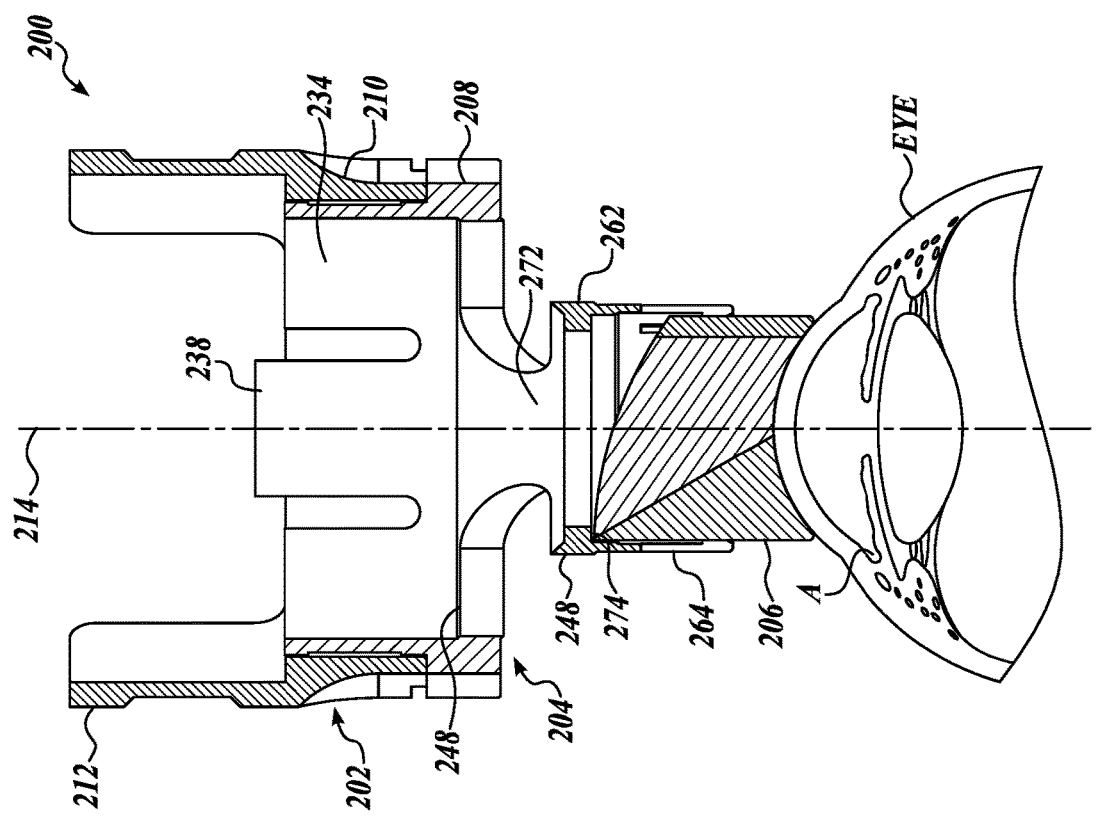
Figure 12:
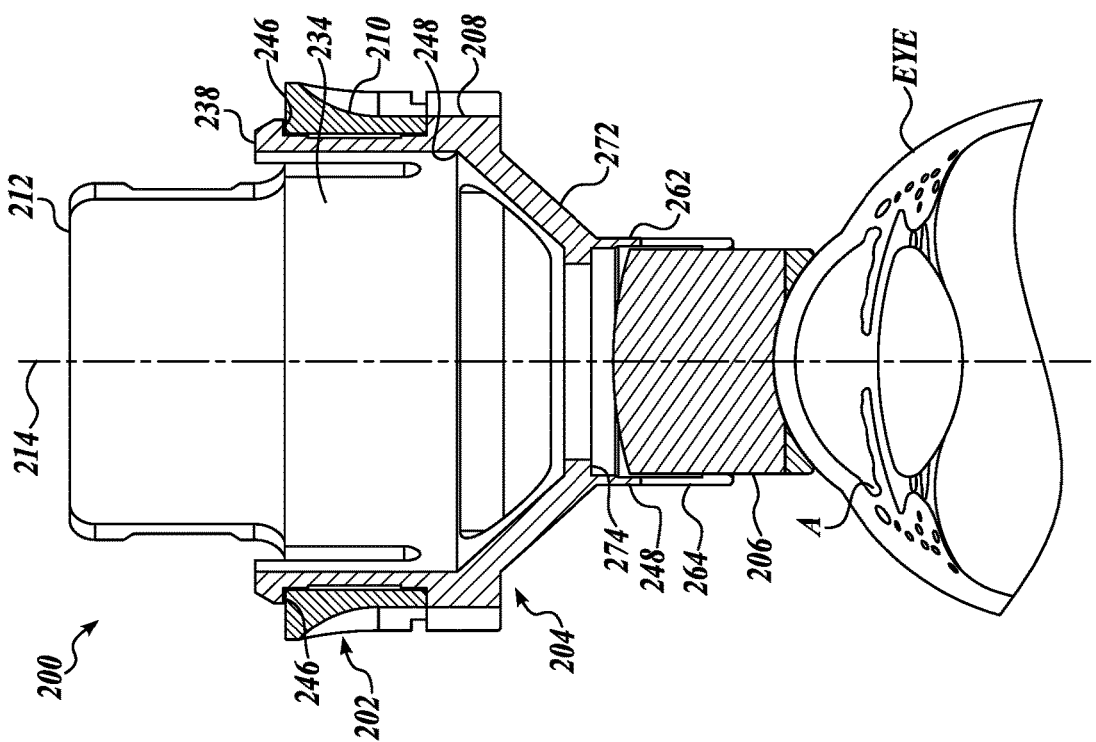

In other embodiments, the lens may be cylindrical in shape (see FIG. 9).

Alignment of Tactile Features

Tactile features 108 and 110 on the respective rotating and holding portions 104 and 102 can be sensed, such as through the fingertips. Particularly, the tactile features 108 of the rotating portion 104 are designed to be alignable with the tactile features 110 of the holding portion 102 through touch and without relying on sight or visual recognition. Referring to FIG. 1, the tactile features 108 of the rotating portion 104 are aligned with the tactile features 110 of the holding portion 102. In FIG. 1, tactile features 108 as indentations are aligned with tactile features 110 which are also indentations. Both indentations 108 and 110 have the same arc length. Particularly, alignment can be judged to have occurred when a side edge 168 of indentation 108 is in line with a side edge 170 of indentation 110.

In the configuration of FIG. 1, the holding portion 102 and rotating portion 104 are aligned at one of the predefined indexing positions. In FIG. 2, the rotating portion 104 is rotated a small amount relative to the holding portion 102 so that the tactile features 108 of the rotating portion 104 are no longer in alignment with the tactile features 110 of the holding portion 102. The rotation of the rotating portion 104 can continue until a user senses that tactile features 108 of the rotating portion 104 are once again in alignment with the tactile features 110 of the holding portion 102.

Method of Operation

To operate the lens indexing assembly 100, the user places the contact surface of the lens 106 on an eye of a patient. Referring to FIG. 1, the user may grasp the holding portion 102 of the lens indexing assembly 100 between the thumb T and index finger I. Because the rotating portion 104 rotates relative to the rest of the holding portion 102, the user can then use the middle finger M on the same hand to rotate the rotating portion 104 and lens 106 while holding the holding portion 102 in a stationary position. The user can pull on the side edge 168 of a tactile feature 108 of the rotating portion 104 until the user senses through touch via the middle finger M that a tactile feature 108 of the rotating portion 104 is aligned with a tactile feature 110 of the holding portion 102 signifying that a predetermined indexing position has been reached.

Using this method, rotation of the lens 106 on the eye of the patient can be accomplished by the user with one hand. In an embodiment, there is no increased resistance from rotating away from the indexing position. Any resistance felt is the inherent friction of contact between plain bearing surfaces in the radial and axial directions. For alignment, the user can rely on one indentation being aligned with another indentation. More specifically, a user may rely on the side edges which start and end at each indentation. For example, in FIG. 1, tactile feature 110 has a side edge 170 and tactile feature 108 has a side edge 168. Side edges 170 and 168 become collinear at the moment of alignment.

Holding the holding portion 102 stationary while the lens 106 is rotated via the rotating portion 104 has advantages. Such rotation technique decreases the chance that the lens 106 will disengage from or be lifted off the eye of the patient. Also, the rotation technique reduces the formation of air bubbles in the fluid between the lens 106 and the eye, which can reflect light and affect the user's ability to evaluate and/or treat the patient's eye.

Even though the holding portion 102 and rotating portion 104 have tactile features 110 and 108 that can be used to achieve the indexing positions through touch alone, this does not preclude the addition of marks that are meant to be visually perceived. For example, the holding portion 102 or the rotating portion 104 or both may include marks on their external surfaces to indicate the beginning or zero position of the 360 degree rotation, as well as subsequent numbered points. For example, suitable markings, such as 0, 1, 2, 3, 4, 5, 6, 7, 8, and 9, may be placed at each tactile feature 108 and 110. Moreover, marks intended for visual perception may be included on the lens 106. Although the marks would not be in focus when the user is examining or treating the ocular anatomy, the marks will define useful start and end points for the user. Also the rotating portion 104 or the holding portion 102 can include a physical stop to prevent the rotation of the collar 104 beyond a certain point. The stop may indicate the 0 degree position in one direction and the 360 degree in the opposite direction. Rotation would not be possible beyond the stop, but rotation would be possible in the direction away from the stop.

In another application, a plurality of indexing marks can be used for relative measurements of ocular structures. For example, if the rotating portion 104 is configured to index every 10 degrees and is used on a lens that has an embedded indicator, as described in U.S. Pat. No. 7,766,480, issued to Graham et al., the disclosure of which is hereby expressly incorporated by reference, the user would be able to estimate the angular size or arc length of ocular structures.

Moreover, in ocular lenses having a plurality of mirrors, for example, four different mirrors in a square or diamond pattern, the rotating portion 104 can be configured to index at four 90 degree angle locations to index with each of the different mirrors. Such indexing in this type of lens will save the user time in accurately rotating the lens to correspond with the desired mirror.

Alternate Embodiments

Referring to FIGS. 7-12, another embodiment of a lens assembly 200 in accordance with the present disclosure is provided. The lens assembly of FIGS. 7-12 is similar in structure as well as function to the previously described lens assembly 100 of FIGS. 1-6, but includes differences regarding the rotating portion 204 and the lens 206, as will be described.

The lens assembly 200 in the illustrated embodiment includes a holding portion 202, a rotating portion 204 configured to rotate on the holding portion 202, and a lens 206 fixedly attached to the rotating portion 204 such that the rotating portion 204 and lens 206 rotate together as a unit. The rotating portion 204 is free to rotate on the holding portion 202 to achieve indexing positions that help the user orient the positioning of the rotating portion 204 and lens 206 relative to the holding portion 202. As described further below, the indexing positions are achieved when tactile features 208 on the rotating portion 204 are in alignment with tactile features 210 on the holding portion 202.

In the illustrated embodiment of FIGS. 7-12, the lens indexing assembly 200 is configured to hold a smaller lens 206 having a cylindrical body. Like the holding portion 104 of FIGS. 1-6, the holding section 260 of the holding portion 204 of FIGS. 7-12 is configured to hold the lens 206 with an interference fit such that the lens 206 can be held in place to rotate with the rotating portion 204 and such that the lens 206 may be removable from the rotating portion 204 for cleaning and sterilization.

Like in the illustrated embodiment of FIGS. 1-6, in the illustrated embodiment of FIGS. 7-12, the holding section 260 includes a crenulated bezel ring 262 comprising a plurality of crenulations or segregated teeth 264 extending from the inner circumference of the rotating portion 204. The lens 206 can be held by a friction fit within the crenulations. The lens 206 may be replaceable. Alternatively, the lens 206 can be held in the bezel ring 262 through an adhesive.

Because the lens 206 in the illustrated embodiment of FIGS. 7-12 is smaller having a smaller diameter and smaller viewing end, the holding section 260 of the holding portion 204 is configured to hold a smaller lens 206. In the illustrated embodiment, a plurality of radial struts 272 extend radially from the inner surface of the holding section 260 to support a holding ring 274. The holding ring 274 supports the crenulated bezel ring 262 comprising a plurality of crenulations or segregated teeth 264. The teeth 264 flex when the lens is inserted such that the lens 206 can be held by a friction fit within the teeth 264. Spacing 276 between the adjacent radial struts 272 allows for light to travel through the center bore of the lens indexing assembly 200 to aid in illumination of the eye.

Lenses 206 may be replaceable. Alternatively, the lens 206 can be held in the bezel ring 262 through an adhesive.

Referring to FIGS. 13-18, another embodiment of a lens assembly 300 in accordance with the present disclosure is provided. The lens assembly of FIGS. 13-18 is also similar in structure as well as function to the previously described lens assembly 100 of FIGS. 1-6, but includes differences regarding the positioning of the holding portion and the rotating portion and differences regarding the tactile features, as will be described.

The lens assembly 300 in the illustrated embodiment of FIGS. 13-18 includes a holding portion 302, a rotating portion 304 configured to rotate on the holding portion 302, and a lens 306 attached to the rotating portion 304 such that the rotating portion 304 and lens 306 rotate together as a unit. The rotating portion 304 is free to rotate relative to the holding portion 302 to achieve indexing positions that help the user orient the positioning of the rotating portion 304 and lens 306 relative to the holding portion 302. As described further below, the rotating portion 304 is configured such that the index finger I of the user (rather than the middle finger M of the previously described embodiments) can be used to rotate the rotating portion 304. In addition, the tactile features 308 on the rotating portion 304 are configured for leverage in rotation and not necessarily for aligning with indentations on the holding portion 302.

In the illustrated embodiment of FIGS. 13-18, the indexing positions are achieved when tactile features 308 on the rotating portion 304 are rotated by a finger on the hand of a user in reference to holding fingers on the hand of a user, as described in greater detail below. The previously described embodiments may also be designed to incorporate the indexing configuration of the illustrated embodiment of FIGS. 13-18.

Figure 14:
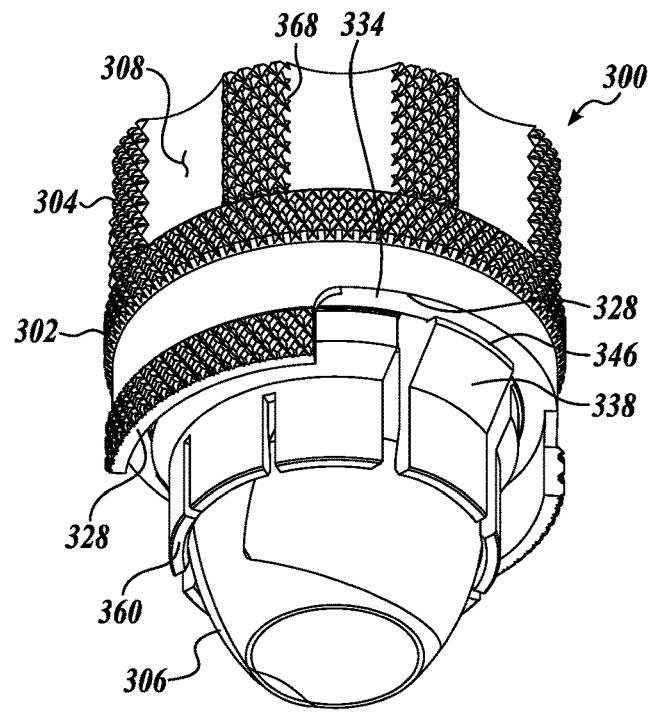
Figure 15:
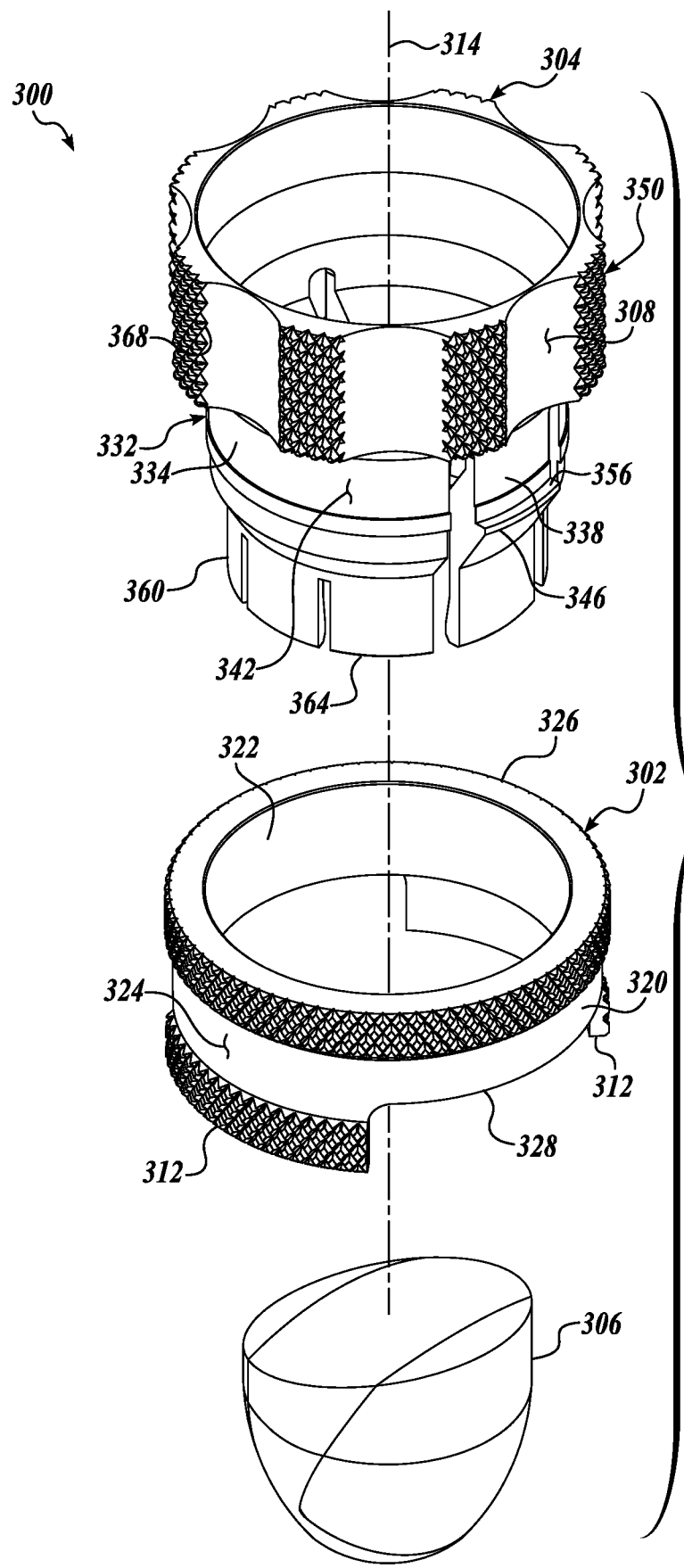

Referring to FIG. 15, the rotating portion 304 includes a first (top) section defining a tactile section 350 including tactile features 308 configured for user rotation and indexing, a second (middle) section defining a coupling section 332 configured for coupling with the holding portion 302, and a third (bottom) section defining a lens holding section 360 configured for holding a lens 306. In contrast with the embodiment of FIGS. 1-6, the first and middle sections of the rotating portion 304 of the illustrated embodiment of FIGS. 13-18 are switched such that, when assembled, the tactile section 350 is located at the top end of the indexing lens assembly 300 above the holding potion 302.

Such configuration of the rotating portion 304 (in contrast with the embodiment of FIGS. 1-6) allows the user to use his or her middle finger M and the thumb T to hold the holding portion 302 of the indexing lens assembly 300, and to use his or her index finger I to rotate the rotating portion 304 of the indexing lens assembly 300.

The index finger is generally the most dexterous and sensitive of the fingers, and therefore, can be a better finger than the middle finger for some users for affecting rotation movement of the rotating portion 302 of the indexing lens assembly 300. Moreover, in this holding configuration with the middle finger M and thumb T holding the holding portion 304 of the indexing lens assembly 300, the indexing finger is further spaced from the patient's head than the middle finger. Such spacing can aid in preventing accidental bumping of the moving finger affecting rotation movement of the rotating portion 302 with the patient's forehead or eye region. However, the different designs of FIGS. 1-6 and 13-18 allow for user selection in rotation finger.

To assembly the lens assembly 300 of FIGS. 13-18, the holding portion 302 is connected to the rotating portion 304 from the bottom end of the rotating portion 304. Referring to FIG. 15, the holding portion 302 is generally comprised of an annular body 320 defining inner and outer surfaces 322 and 324 and top 326 and bottom 328 axial surfaces. The annular body 320 defines an inner bore having a central axis 314 to permit viewing through the holding portion 302 to the lens 306 when the lens indexing assembly 300 is assembled.

Figure 13:
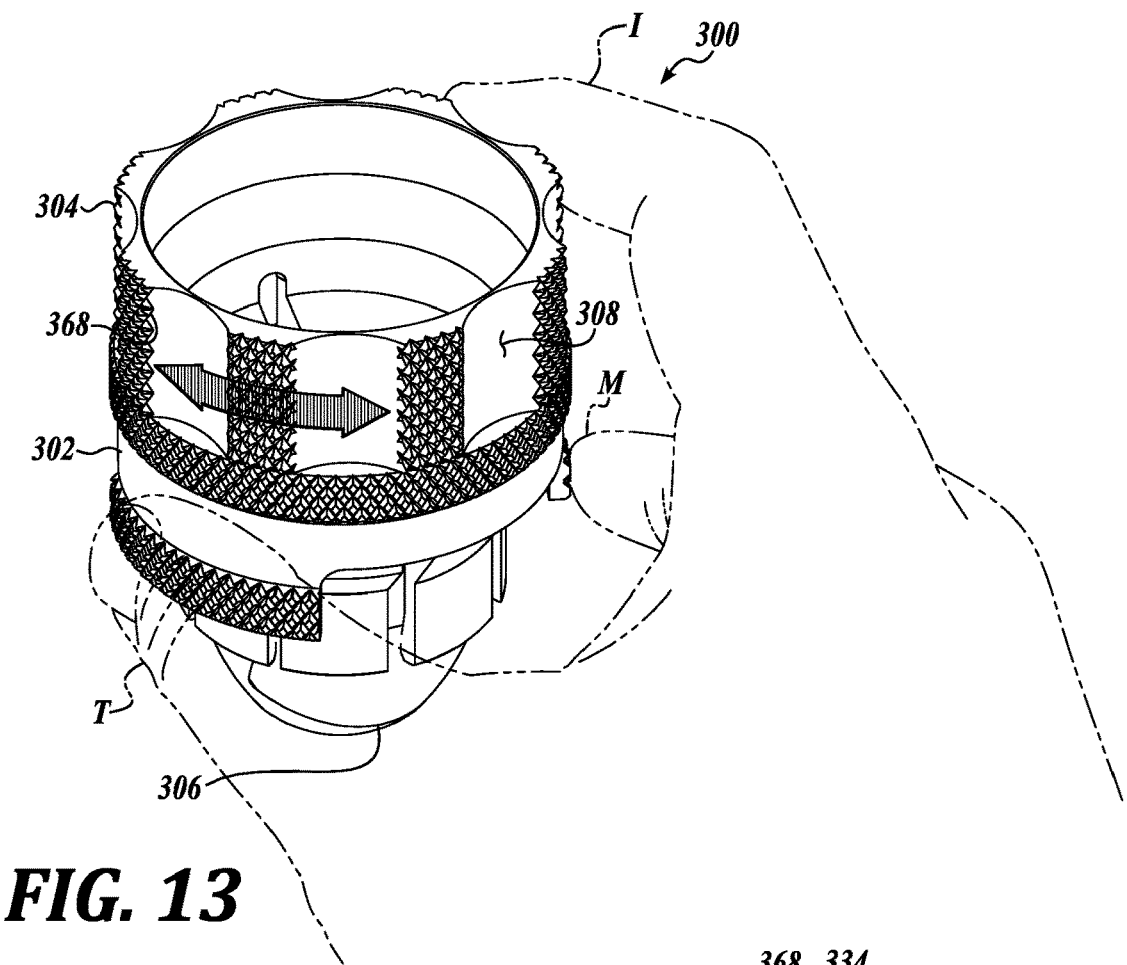
FIGS. 13-18 are diagrammatical illustrations of a lens assembly, similar to the diagrammatical illustrations in FIGS. 1-6, but in accordance with another embodiment of the present disclosure.
Figure 18:
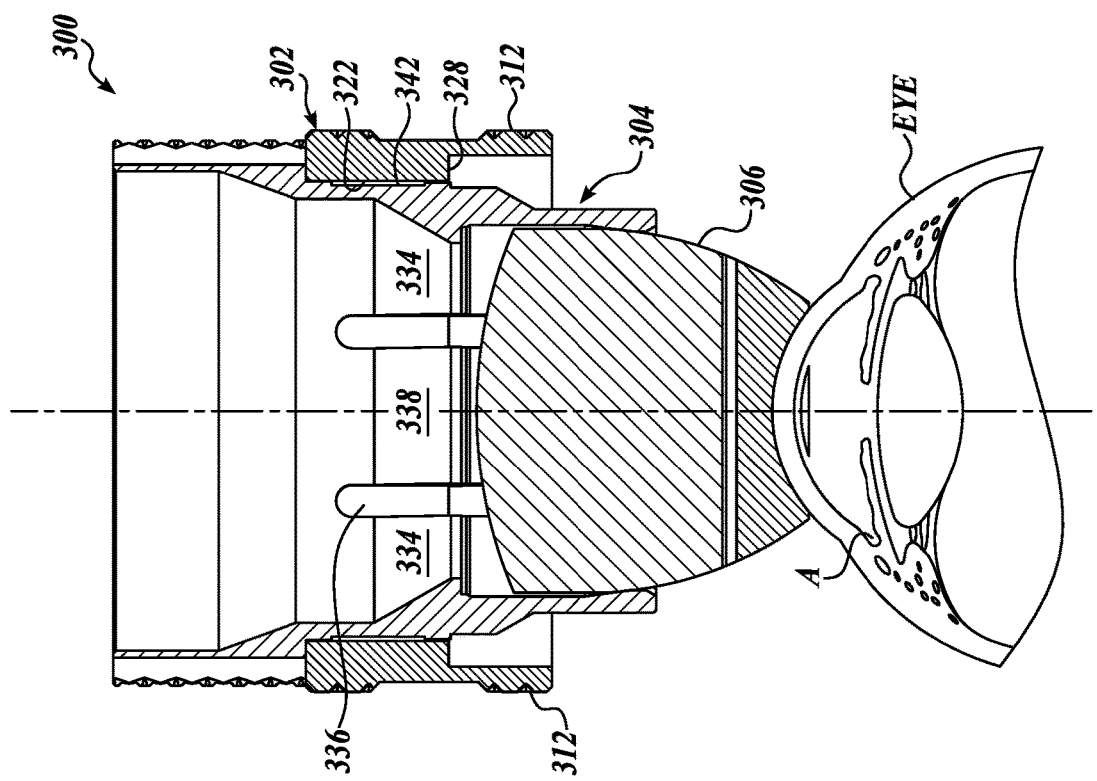

Extending from the bottom axial surface 328 of the holding portion 302, the holding portion 302 of the illustrated embodiment further includes extended holding tabs 312 to allow the user to grip the holding portion, for example, with a thumb and middle finger, as shown in FIG. 13. As best seen in FIG. 18, the holding tabs 312 are spaced on the outer edge of the bottom axial surface 328 of the holding portion 302, so as not to interfere with the rotation of the rotation portion 304 relative to the holding portion 302, as described in greater detail below.

As described above, the second (middle) section of the rotation portion 304 includes a coupling section 332 configured for coupling with the holding portion 302. The coupling section 332 of the rotation portion 304 is a cylindrical section including a plurality of partial cylindrical segments 334 and 338 extending from the annular body 330, all of similar inner and outer radiuses in a circular arrangement, configured for coupling the rotation portion 304 with the holding portion 302. First and second cylindrical segments 334 and 338 each have an outer surface 342 which functions as a radial plain bearing surface that is configured to rotate against the inner plain bearing surface 322 of the holding portion 302 when the rotation portion 304 and the holding portion 302 are coupled together. The outer surface 342 is of a slightly smaller radius than the inner surface 322 of the holding portion 302 to allow for coupling of the two portions 302 and 304 (see FIGS. 17 and 18).

Figure 16:
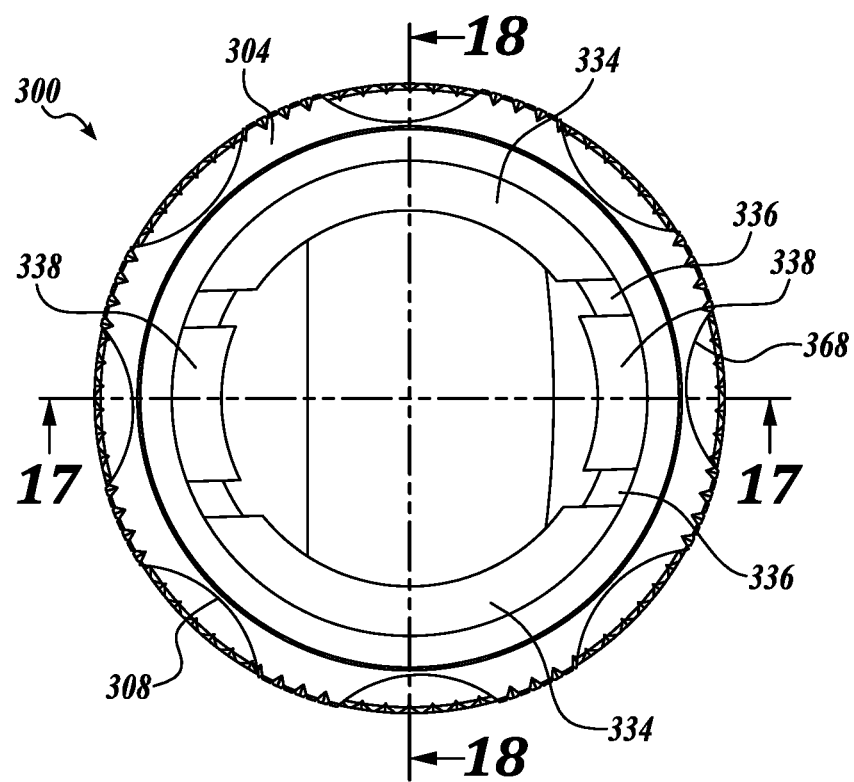

The first and second cylindrical segments 334 may be considered rigid or semi-rigid, while the third and fourth cylindrical segments 338 may be considered to be more flexible than the first and second segments 334. In the illustrated embodiment, the first and second segments 334 make up a majority of the circumference in order to be rigid, while the third and fourth segments 338 make up a smaller portion of the total circumference, which allows the third and fourth segments 338 to flex relative to the first and second segments 334. As can be seen in FIG. 16, the first and second segments 334 are larger than the third and fourth segments 338. Recesses 336 between adjacent segments allow the third and fourth segments 338 to flex relative to the first and second segments 334.

In some embodiments, the rigid and flexible segments may be made from the same material. In other embodiments, the rigid and flexible segments may be made from different materials to provide for a difference in flexibility.

The flexible segments 338 make up a portion of the radial plain bearing surface 342 (see FIG. 15). However, a function of the segments 338 is to keep the rotating portion 304 axially aligned with the holding portion 302 when two are coupled together. In the illustrated embodiment, each flexible segment 338 includes an outwardly extending radial barb 346. The radial barb 346 has an upper surface 356 that makes contact with the bottom axial surface 328 of the holding portion 302 to keep the rotating portion 304 axially aligned within the holding portion 302.

As seen in FIG. 14, the bottom axial surface 328 of the holding portion 302 in the illustrated embodiment extends around a portion of the annular wall 320 of the holding portion 302, allowing for 360 degree rotation of the rotation portion 304 relative to the holding portion 302. In other embodiments, the holding portion 302 may designed for other rotation parameters up to 360 degree rotation. For example, the holding tabs 312 of the holding portion 302 could be designed to limit rotation of the rotating portion 304 relative to the holding portion 302 within certain rotation limits, such as 90 degree rotation.

Further, the flexible cylindrical segments 338 also render the rotating portion 304 separable from the holding portion 302. First, to attach the rotating portion 304 to the holding portion 302, the flexible segments 338 can be depressed radially so that the radial barbs 346 clear the inner radius of the inner wall surface 322 of the holding portion 302. While the flexible segments 338 of the rotating portion 304 are depressed, the holding portion 302 is slipped onto the rotating portion 304 such that the plain bearing surface 342 of the rotating portion 304 is mated against the inner plain bearing surface 322 of the holding portion 302. When coupled, a top radial surface of the radial barbs 346 is in close proximity with the bottom axial surface 328 of the holding portion 302 (see FIG. 14). To release, the radial barbs 346 can be depressed radially and the rotating portion 304 can be decoupled from the holding portion 302.

Referring to FIG. 14, the holding section 360 is configured to hold the lens 306 with an interference fit such that the lens 306 can be held in place to rotate with the rotating portion 304 and such that the lens 306 may be removable from the rotating portion 304 for cleaning and sterilization.

In the illustrated embodiment, the holding section 360 includes a bezel ring 362 comprising a plurality of crenulations or segregated teeth 364 extending from the inner circumference of the rotating portion 304 (see FIGS. 17 and 18), similar to previously described embodiments. The teeth 364 flex when the lens 306 is inserted such that the lens 306 can be held by a friction fit within the crenulations. In the illustrated embodiment, the ends of the flexible segments 338 are a part of the teeth 364 of the lens holding portion 360.

Figure 17:
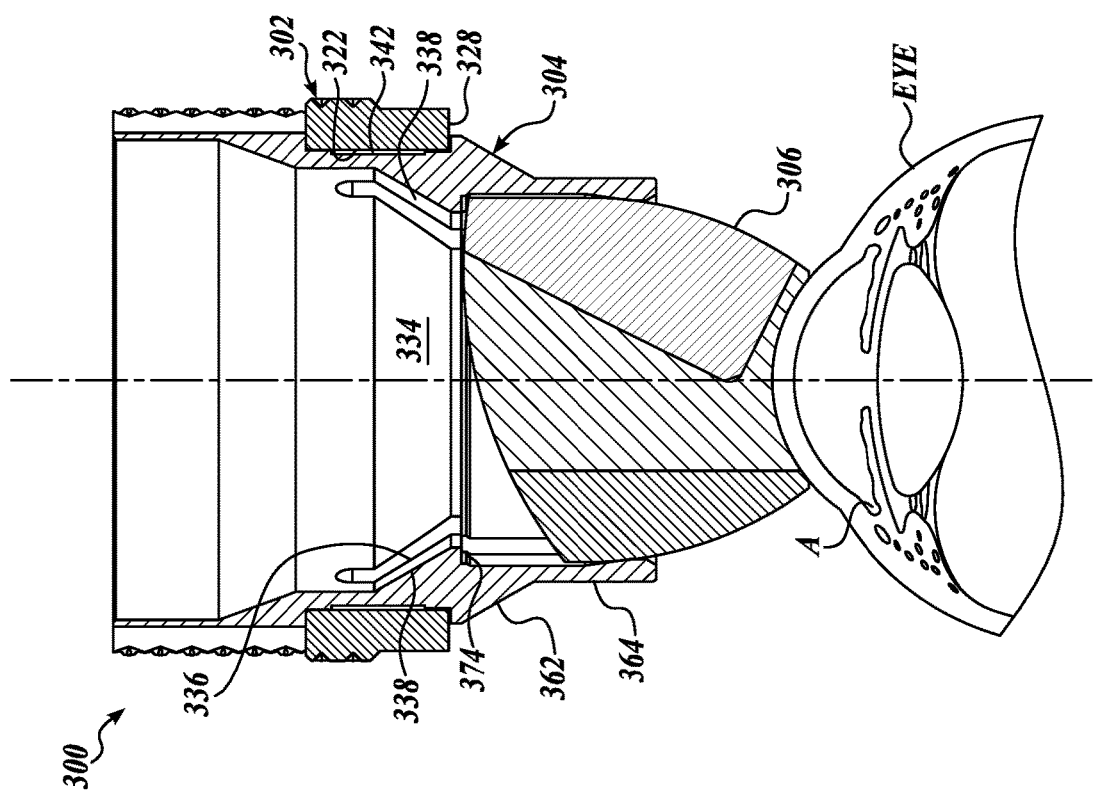
Figure 19:
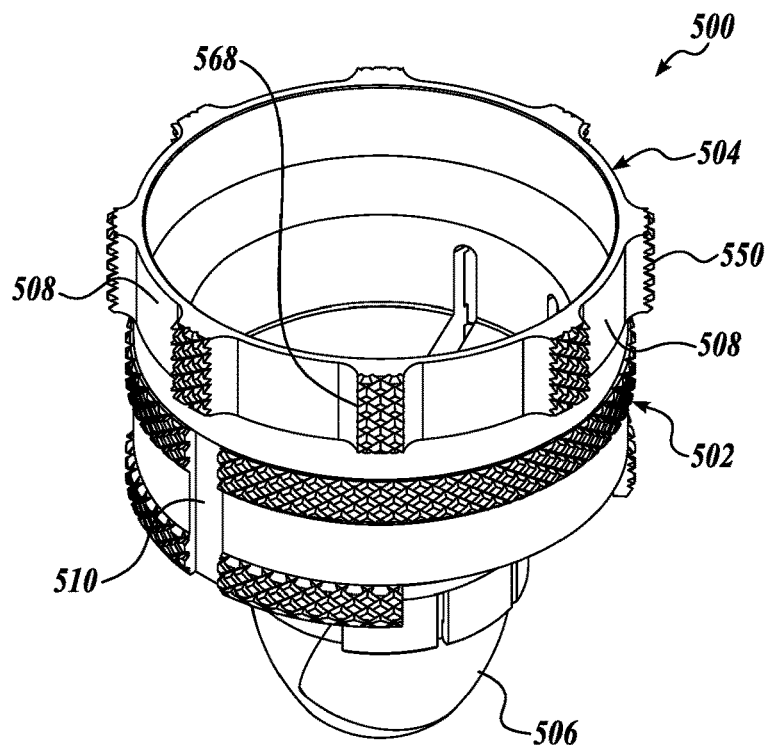
FIGS. 19-24 are diagrammatical illustrations of a lens assembly, similar to the diagrammatical illustrations in FIGS. 13-18, but in accordance with another embodiment of the present disclosure.
Figure 20:
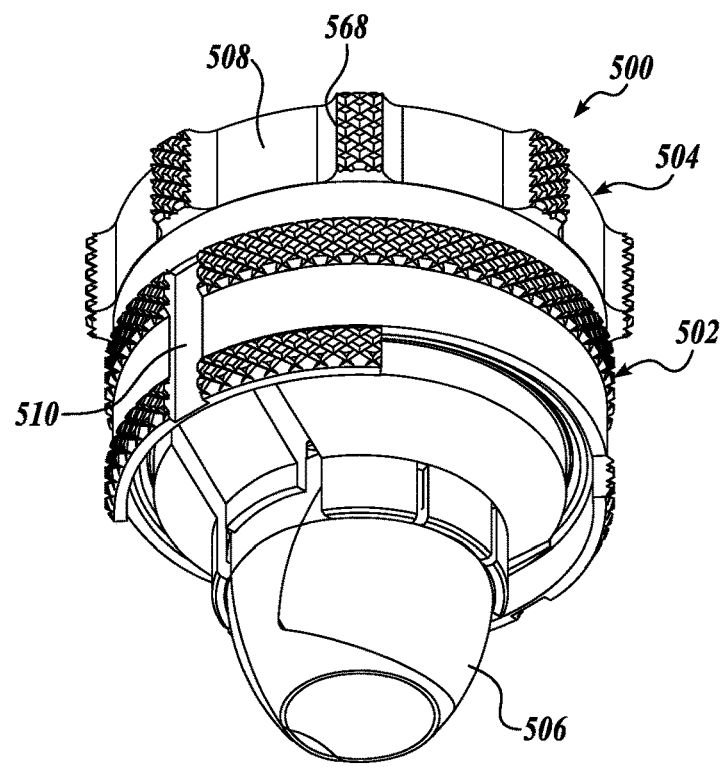
Figure 21:
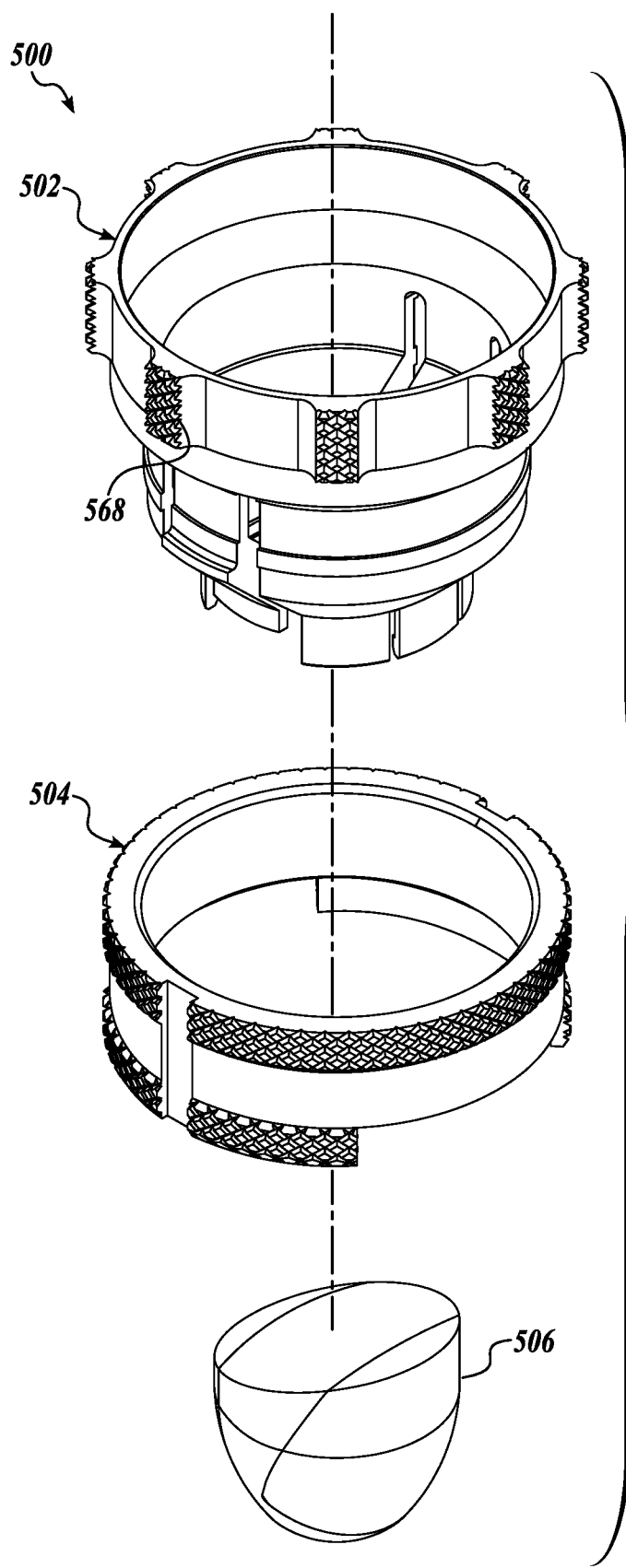
Figure 22:
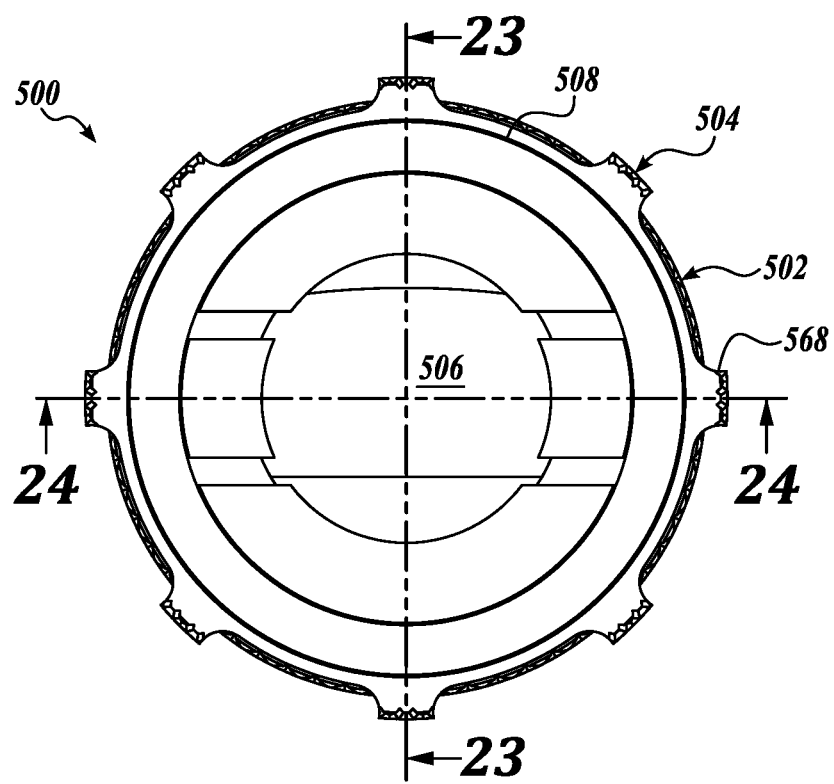
Figure 24:
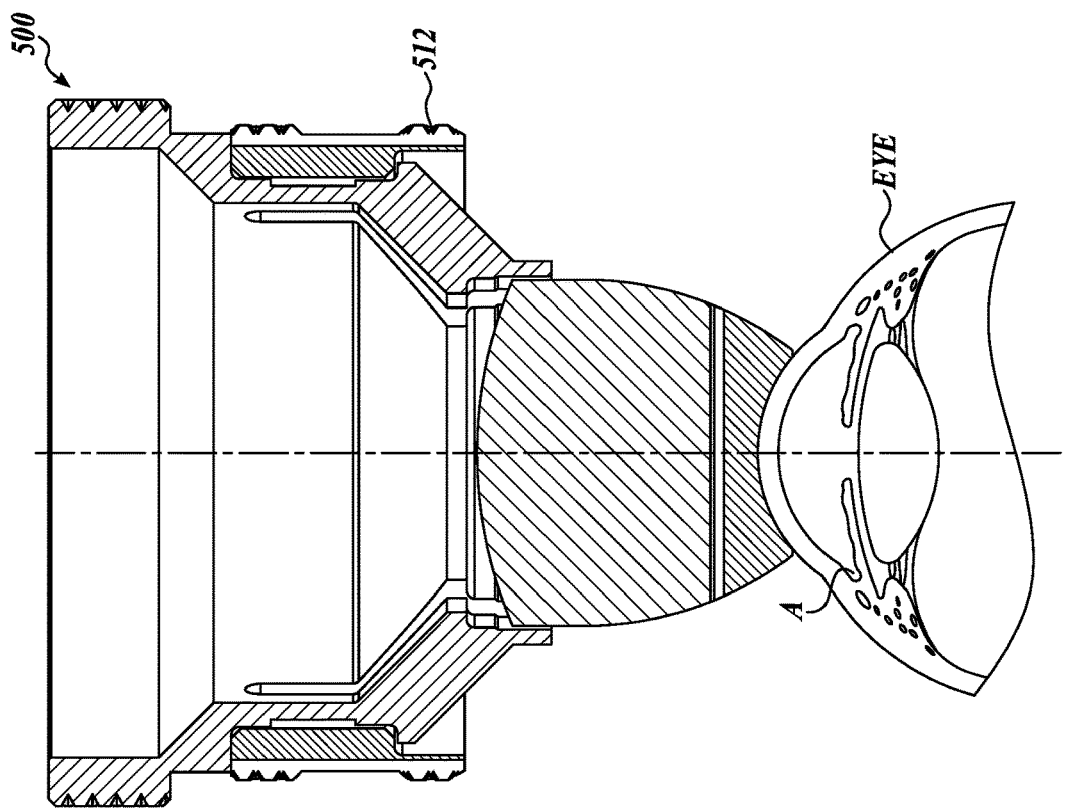
Figure 23:
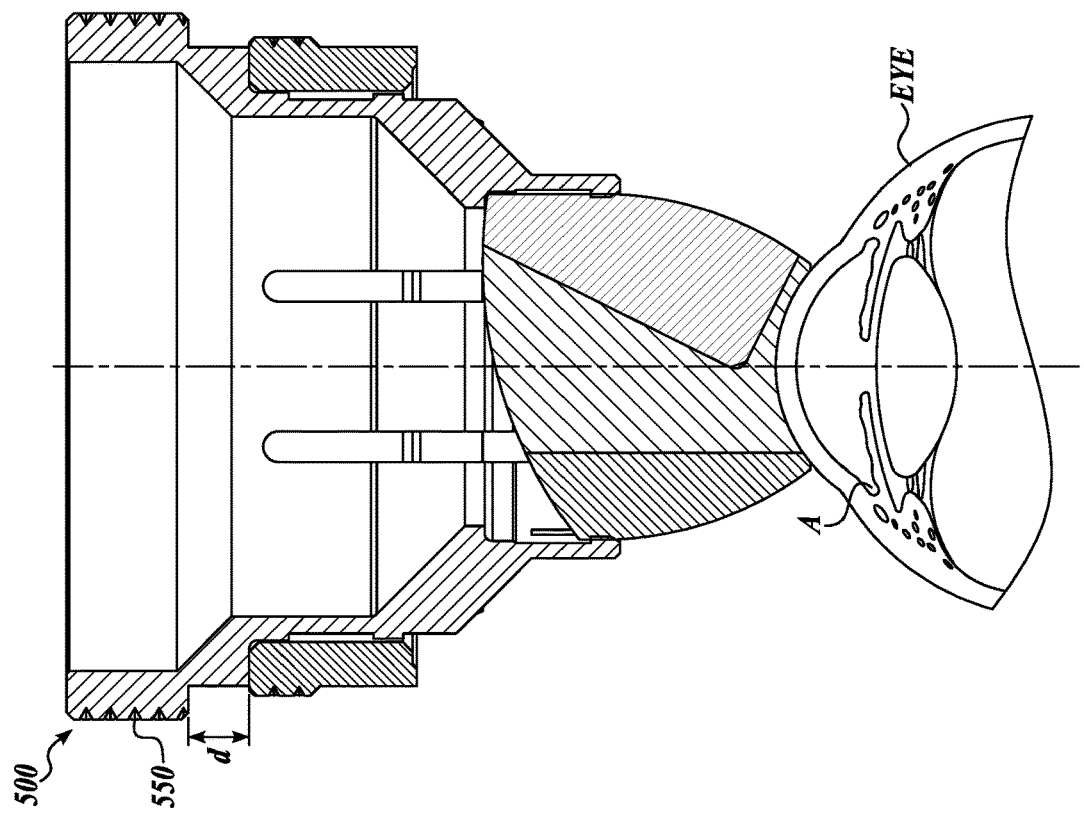

As seen in FIGS. 17 and 18, an inwardly extending stopping protrusion 374 keeps the lens 306 from being inserted past the holding section 360.

In the illustrated embodiment of FIGS. 13-18, unlike the previously described embodiments, the holding portion 302 does not include tactile features defining indentations. In contrast, only the rotating portion 304 includes tactile features 308 on the outer surface of the rotating portion 304.

Instead of indexing being achieved by aligning adjacent tactile features on the holding portion and the rotating portion, as seen in the previously described embodiments, indexing in the illustrated embodiment of FIGS. 13-18 is achieved by the user's knowledge of a starting position with his or her moving finger and knowing the new position on the moving finger. Indexing also may be achieved by the user's knowledge of a starting position with his or her moving finger and a subsequent visual position of the user's moving finger on the circumference of the eye. For example, the user may start with the index finger I at a 12 o'clock position, the middle finger M adjacent the index finger I, also at a 12 o'clock position, and the thumb at a 6 o'clock position. The user's middle finger M and thumb T remain in the same positions on the holding portion 302. However, the user may move the index finger I and the rotating portion 304 from the 12 o'clock position to a 2 o'clock position to adjust the view of the patient's eye.

Indexing is understood by the user feeling the new relative positioning of the index finger I relative to the middle finger M and/or by visual inspection of the relative positioning of the index finger I relative to the middle finger M.

In the illustrated embodiment, both the holding portion 302 and the rotating portion 304 include optional knurled sections to improve the user's grip on the lens assembly 300. Such knurled sections may be combined with smooth surfaces to improve grip, as seen in the illustrated embodiment. In other embodiments, other sections may be knurled based on ergonomic design.

In the illustrated embodiment, and in all the embodiments described herein, the tactile features 308 on the rotating portion 304 provide leverage for the rotating finger. In that regard, the tactile features 308 on the rotating portion 304 are shown as indentations on the outer surface of the rotating portion 304. Each tactile feature 308 has side edges 368 on either side of each of the indentations. Depending on the direction of rotation, the user can pull or push on these side edges 368 to effect rotation of the rotating portion 304 relative to the holding portion 302.

Referring to FIGS. 19-24, another embodiment of a lens assembly 500 in accordance with the present disclosure is provided. The lens assembly of FIGS. 19-24 is in many respects similar in structure as well as functions to the previously described lens assembly 300 of FIGS. 13-18, but includes differences regarding the tactile features, as will be described.

In the illustrated embodiment, the holding portion 502 of the lens assembly 500 includes at least one tactile feature 510, which allows the user to orient the position of the rotation portion 504 of the lens assembly 500 with the tactile feature 510. For example, if the user is rotating the rotating portion 504 forward to a certain position at a certain degree of rotation, then the user wants to return to the original position, the user can use the at least one tactile feature 510 on the holding portion 502 to return the rotating portion 504 to an original position.

In addition, the tactile section 550 of the rotating portion 504 in the illustrated embodiment of FIGS. 19-24 has a smaller height profile as compared to the embodiment of FIGS. 13-18, allowing for a more compact design. In addition, the tactile section 550 is spaced from the holding portion by distance d (see FIG. 23), the tactile features on the rotating portion are configured to be of a different cross-sectional shape, and the sizing of the indexing lens assembly is different, all to improve the ergonomic design for a specific user.

Figure 25:
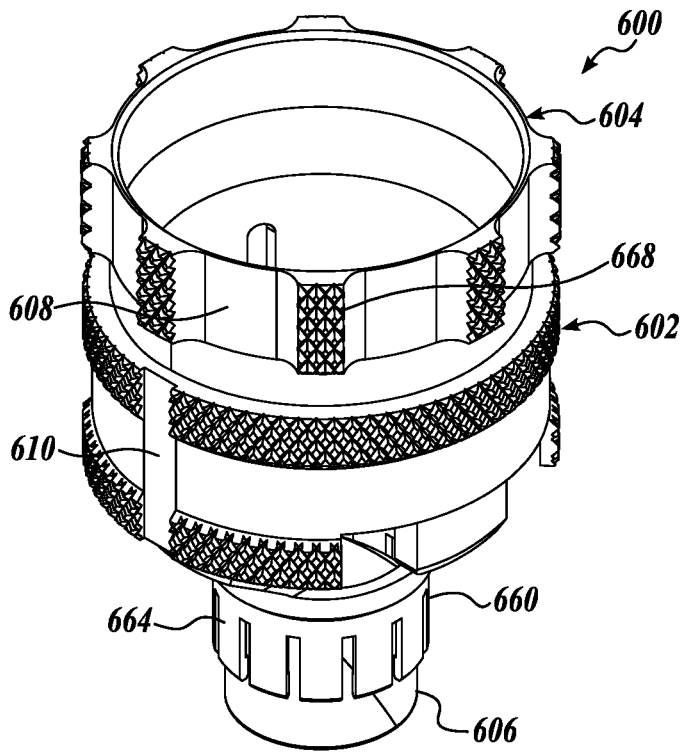
FIGS. 25-30 are diagrammatical illustrations of a lens assembly, similar to the diagrammatical illustrations in FIGS. 19-24 and FIGS. 7-12, but in accordance with another embodiment of the present disclosure.
Figure 26:
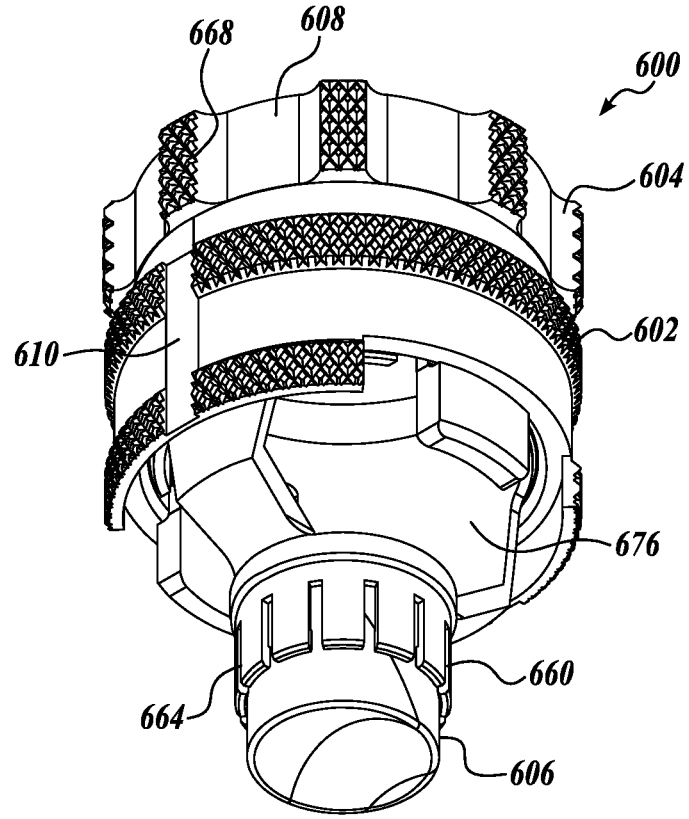
Figure 27:
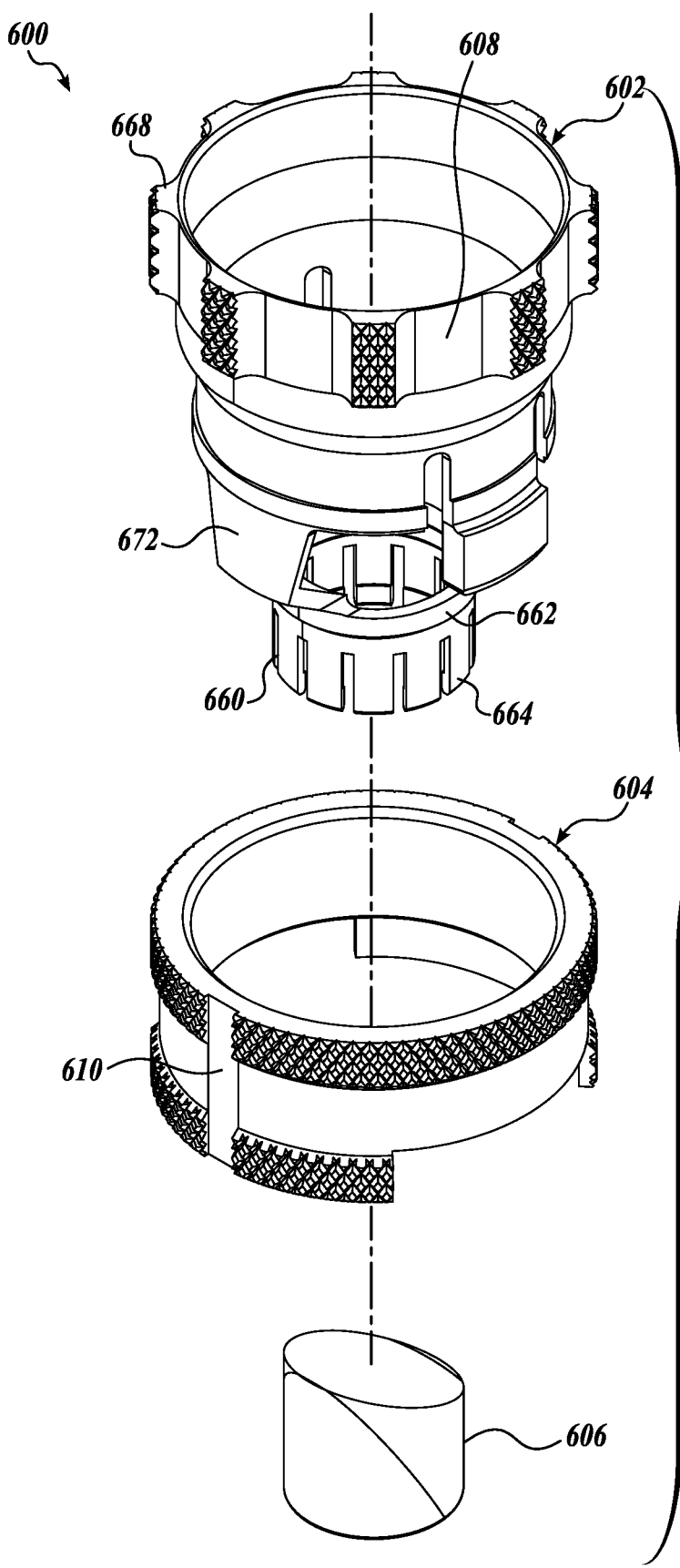
Figure 28:
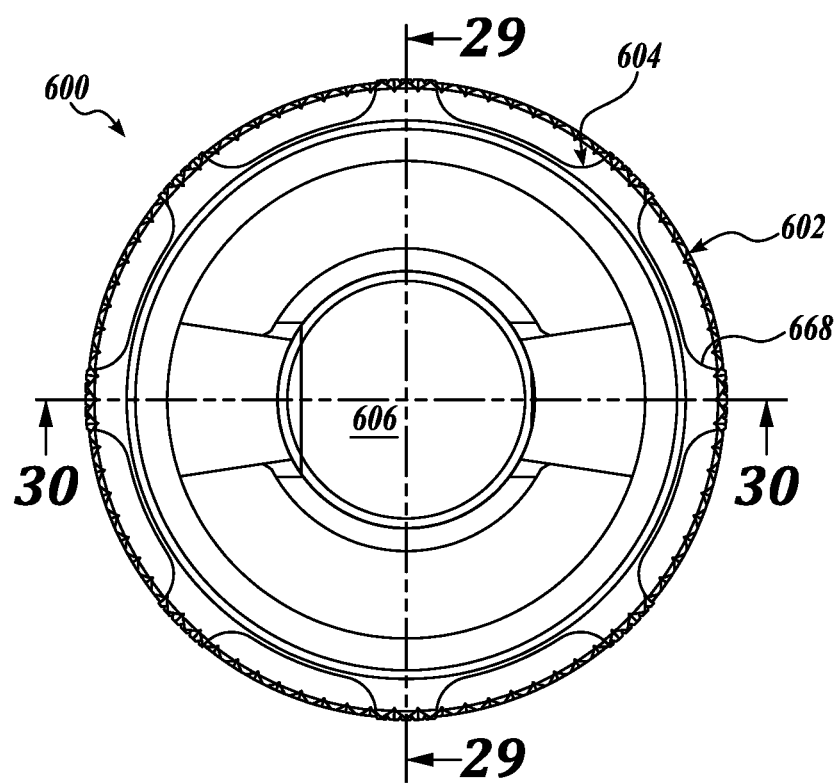
Figure 30:
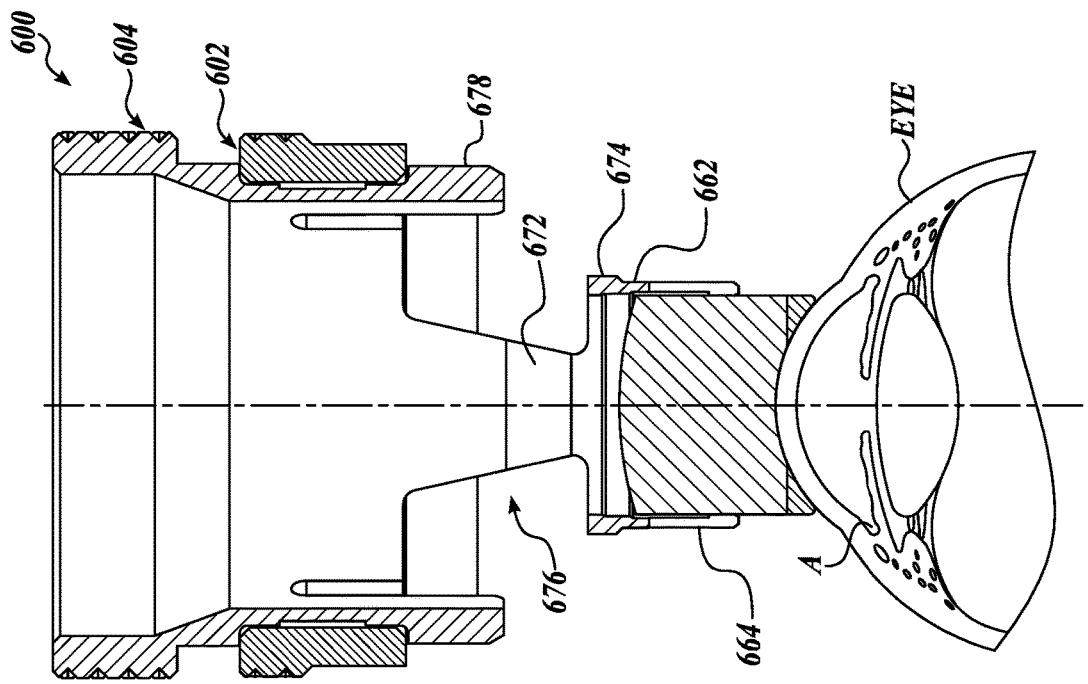
Figure 29:
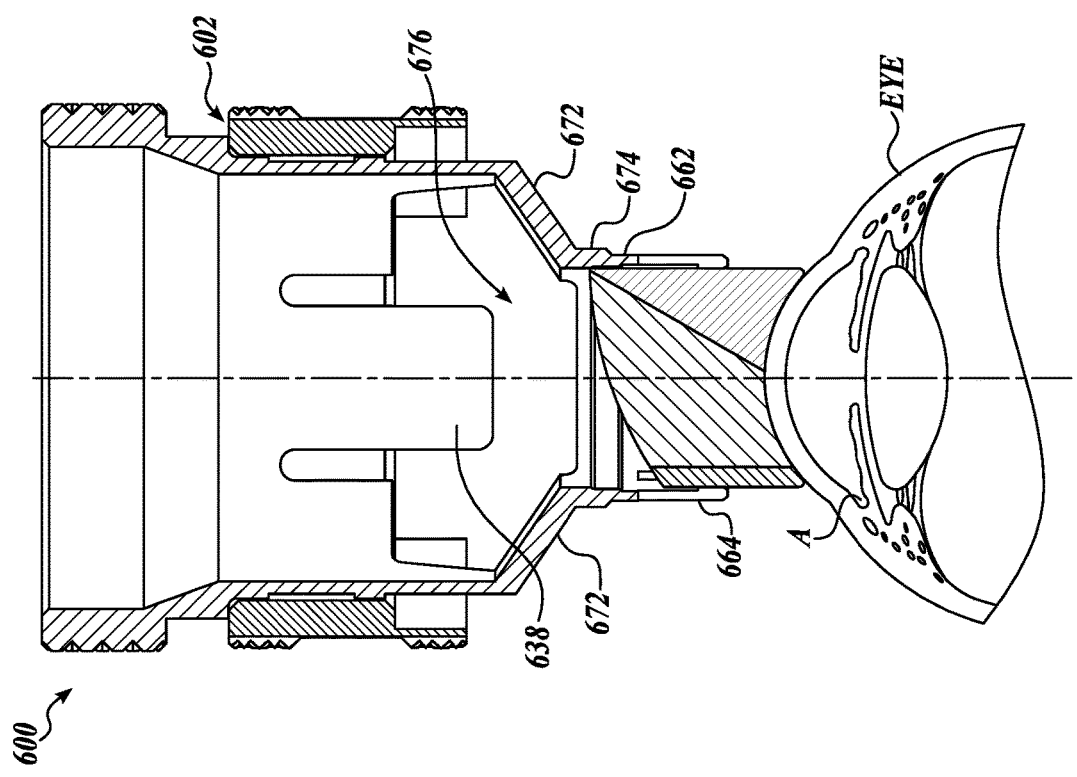

Referring to FIGS. 25-30, another embodiment of a lens assembly 600 in accordance with the present disclosure is provided. The lens assembly of FIGS. 25 30 is in many respects similar in structure as well as functions to the previously described lens assembly 500 of FIGS. 19-24, but includes differences regarding the lens, as will be described.

The lens 606 of the illustrated embodiment of FIGS. 25-30 is the same as the lens 206 in FIGS. 7-12. Because the lens 606 in the illustrated embodiment of FIGS. 25-30 is smaller than the lens 506 of FIGS. 19-24, having a smaller diameter and smaller viewing end, the holding section 660 of the rotating portion 604 is configured to hold a smaller lens 606. In the illustrated embodiment, a plurality of radial struts 672 extend radially from the inner surface of the holding section 660 to support a holding ring 674. The holding ring 674 supports the crenulated bezel ring 662 comprising a plurality of crenulations or segregated teeth 664. The teeth 664 flex when the lens is inserted such that the lens 606 can be held by a friction fit within the teeth 664. Spacing 676 between the adjacent radial struts 672 allows for light to travel from through the center bore of the lens indexing assembly 600 to aid in illumination of the eye.

Different from the embodiment of FIGS. 13-18, the ends of the flexible segments 638 are not part of the teeth 664 of the lens holding section 660. Instead the flexible segments 638 extend in the spacing 676 between the adjacent radial struts 672 of the lens holding section 660.

Figure 31:
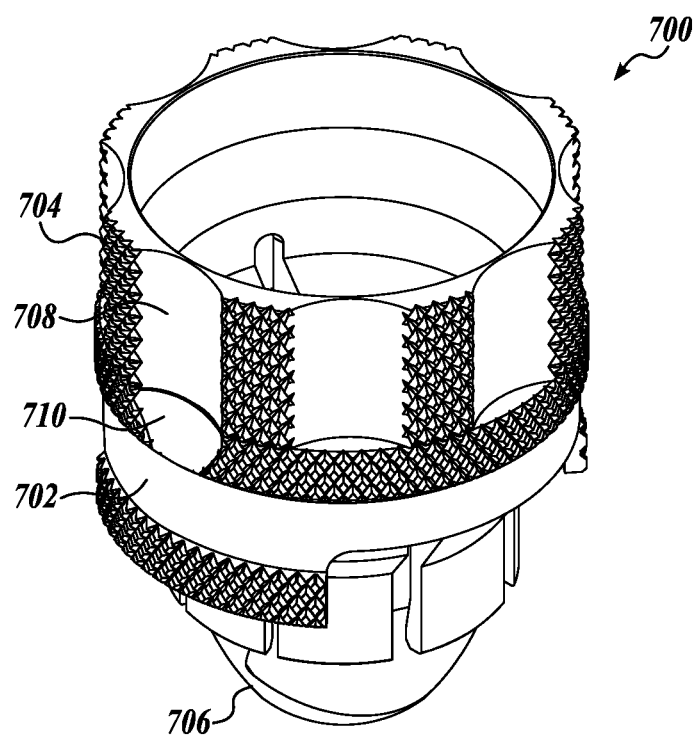
FIGS. 31-33 are diagrammatical illustrations of a lens assembly, similar to the diagrammatical illustrations in FIGS. 13-15, but in accordance with another embodiment of the present disclosure.
Figure 32:
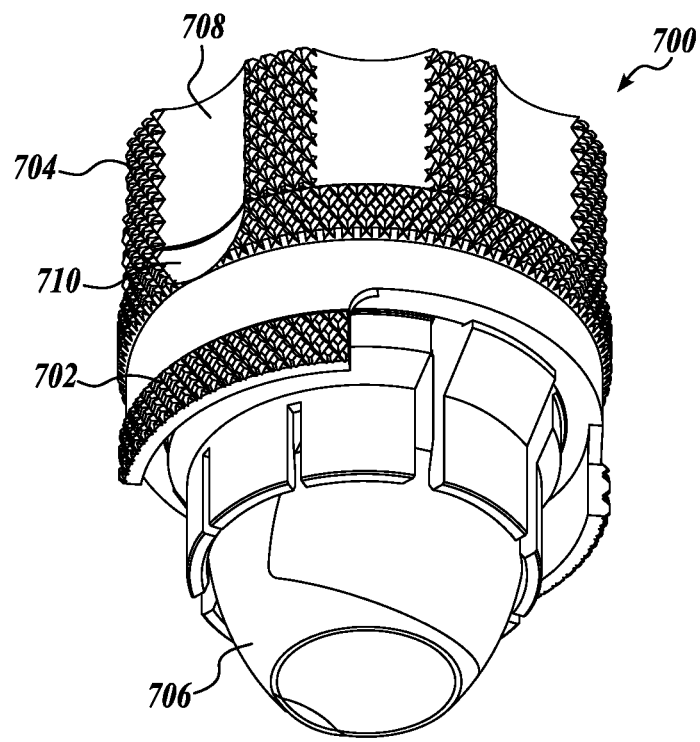
Figure 33:
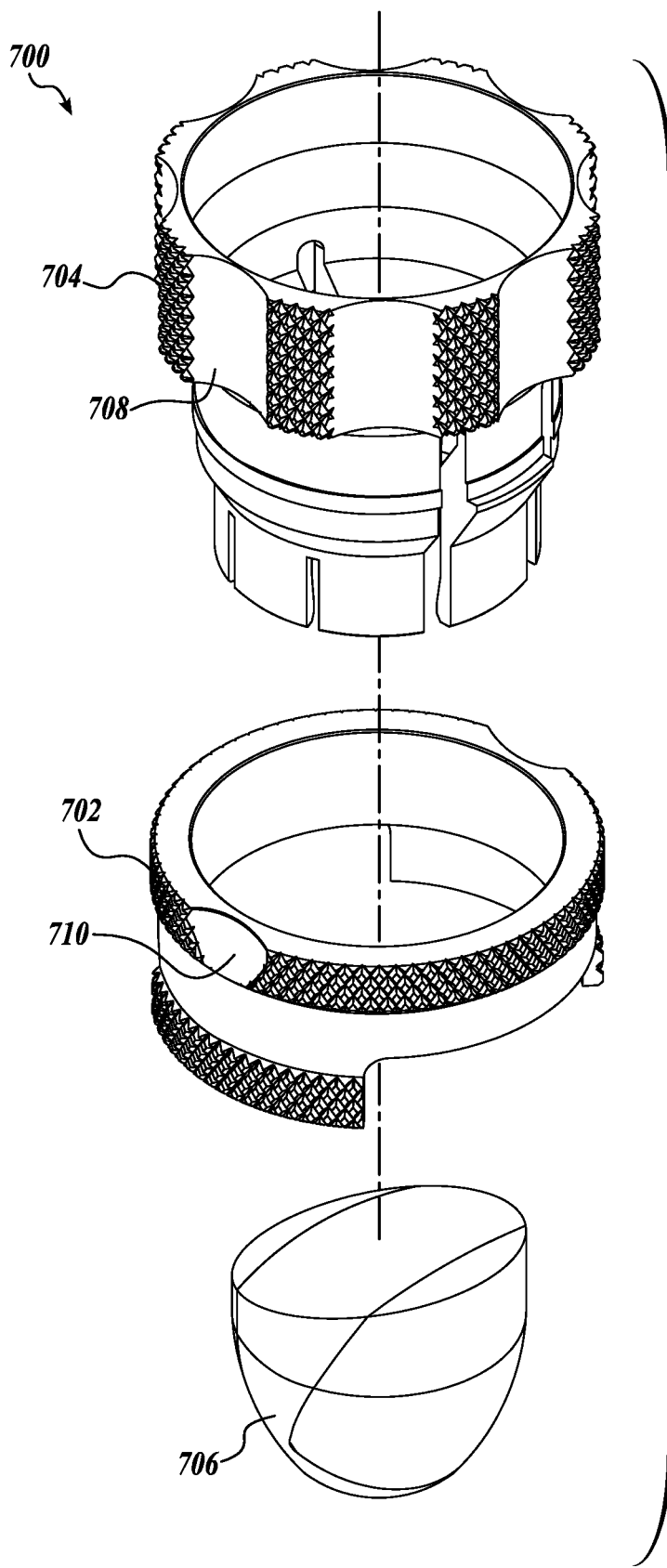
Figure 34:
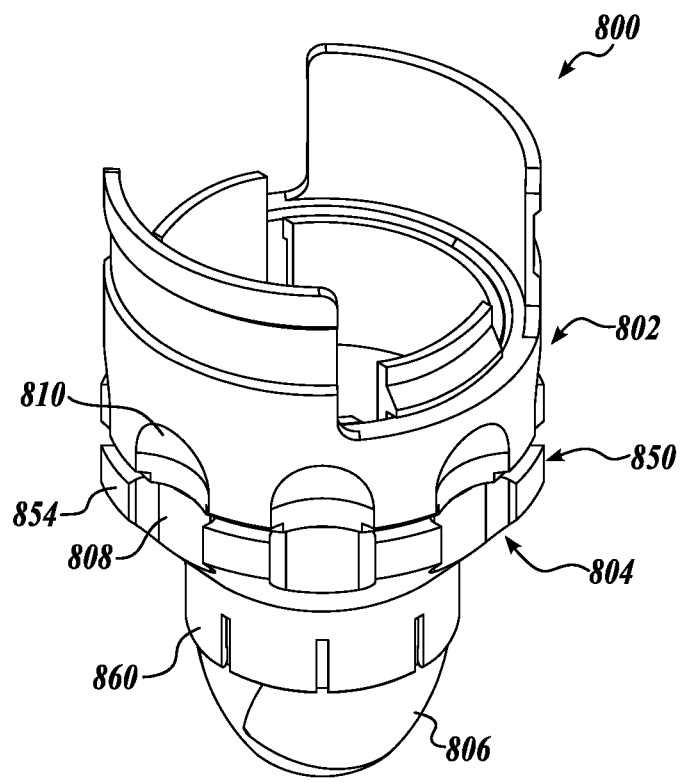
FIGS. 34-37 are diagrammatical illustrations of a lens assembly, similar to the diagrammatical illustrations in FIGS. 1-6, but in accordance with another embodiment of the present disclosure.
Figure 35:
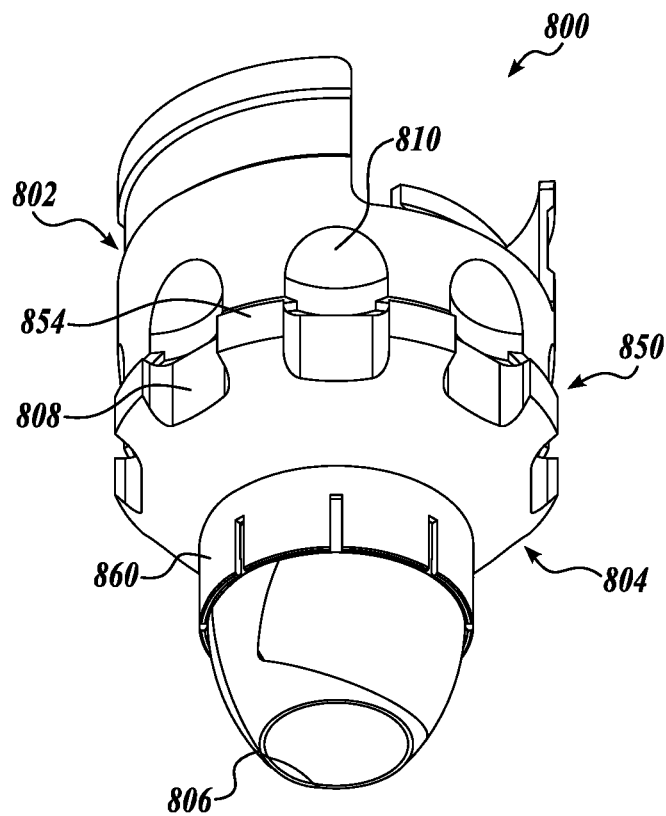
Figure 36:
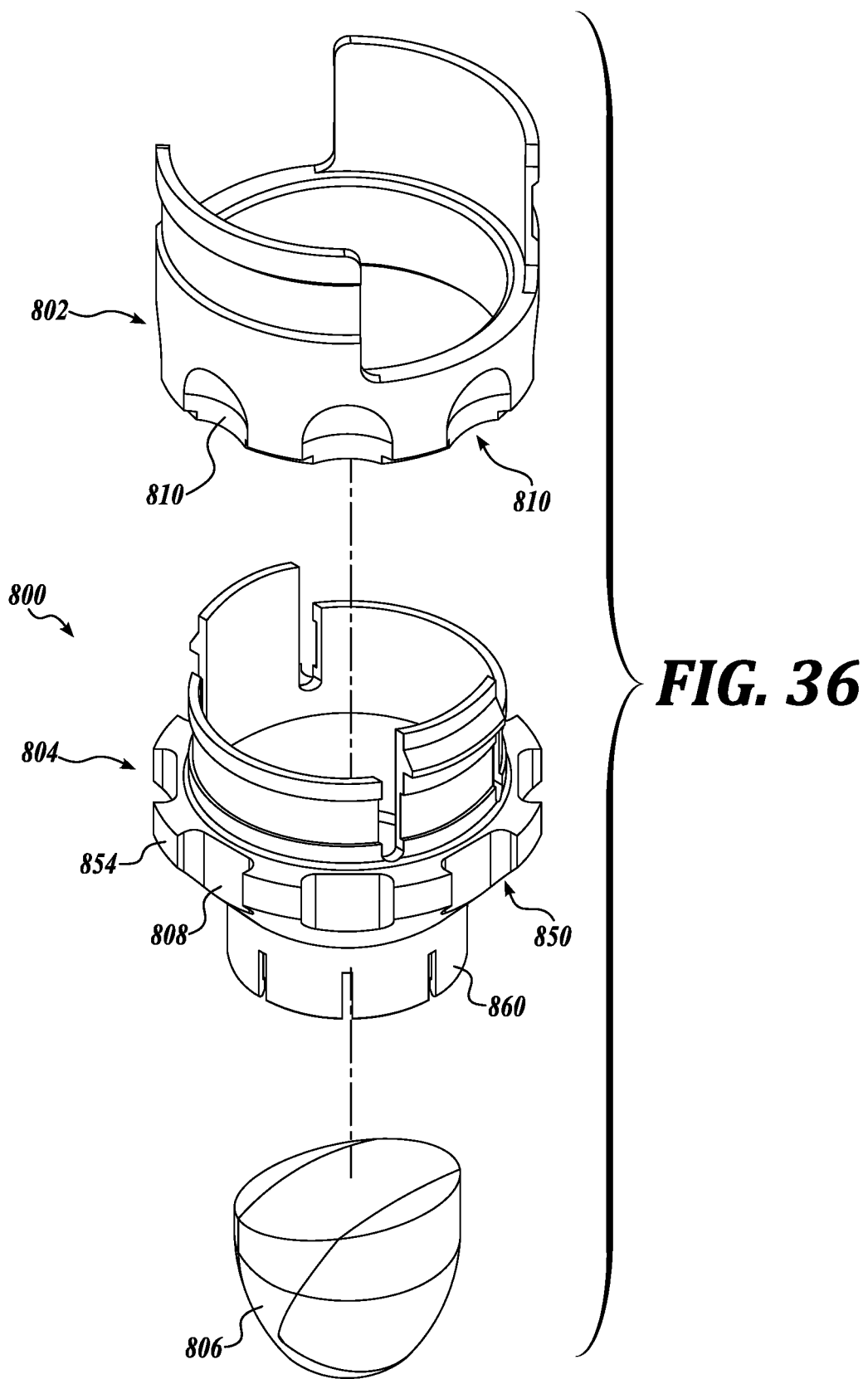

Referring to FIGS. 31-33, another embodiment of a lens assembly 700 in accordance with the present disclosure is provided. The lens assembly of FIGS. 31-33 is in many respects similar in structure as well as functions to the previously described lens assembly 300 of FIGS. 13-15, but includes differences regarding the tactile features, as will be described.

In the illustrated embodiment of FIGS. 13-18, the holding portion 302 does not include tactile features defining indentations; only the rotating portion 304 includes tactile features 308 on the outer surface of the rotating portion 304. In contrast, in the illustrated embodiment of FIGS. 31-33, the holding portion 702 of the lens assembly 700 includes a tactile feature 710 for mating with the tactile features 708 of the rotating portion. Like previously described tactile features, the tactile features 710 of the illustrated embodiment comprise indentations defined to receive the fingertip of a user. Such tactile features can be referred to as "fingertip grooves" because they are configured to accommodate the size and shape of an average finger.

Referring to FIGS. 34-37, another embodiment of a lens assembly 800 in accordance with the present disclosure is provided. The lens assembly of FIGS. 34-37 is similar in structure as well as function to the previously described lens assemblies, including lens assembly 100 of FIGS. 1-6, but includes differences regarding the rotating portion 804, as will be described. It will be appreciated that the rotating portion 804, or features thereof, can be employed with any embodiment described herein.

The lens assembly 800 in the illustrated embodiment includes a holding portion 802, a rotating portion 804 configured to rotate on the holding portion 802, and a lens 806 fixedly attached to the rotating portion 804 such that the rotating portion 804 and lens 806 rotate together as a unit. The rotating portion 804 is free to rotate on the holding portion 802 to achieve one or more positions, such as indexing positions, that help the user orient the positioning of the rotating portion 804 and lens 806 relative to the holding portion 802. The indexing positions are achieved, for example, when tactile features 808 on the rotating portion 804 are in alignment with tactile features 810 on the holding portion 802.

Like in the illustrated embodiment of FIGS. 1-6, in the illustrated embodiment of FIGS. 34-37, the rotating portion 804 includes a first (top) section defining a coupling section configured for coupling with the holding portion 802, a second (middle) section defining a tactile section 850 including tactile features 808 configured for aligning with the tactile features 810 on the holding portion 802, and a third (bottom) section defining a lens holding section 860 configured for holding a lens 806.

Like the holding portion 104 of FIGS. 1-6, the holding section 860 of the holding portion 804 of FIGS. 34-37 is configured to hold the lens 806 with an interference fit such that the lens 806 can be held in place to rotate with the rotating portion 804 and such that the lens 806 may be removable from the rotating portion 804 for cleaning and sterilization. The lens 806 can be held by a friction fit. The lens 806 may be replaceable. Alternatively, the lens 806 can be held via an adhesive.

In the illustrated embodiment, the tactile features 808 are indentations in the outer surface 854 of the rotating portion 804. In some embodiments, tactile features 808 can be any surface contours, such as indentations, that differ with respect to radius from the outer radius of the outer surface 854.

In the illustrated embodiment, the tactile features 808 comprise indentations defined to receive the fingertip of a user. In the illustrated embodiment, the tactile features 808 have U-shaped (e.g., slightly rounded in some embodiments) indentations. In some embodiments, the U-shape of the indentations is pronounced, such that the indentations are substantially similar to a square or rectangle (with an open top for receiving part of the fingertip) or identical to a square or rectangle. In other words, the indentations are formed as outwardly facing, U-shaped channels, each having a bottom wall and two side walls.

Figure 37:
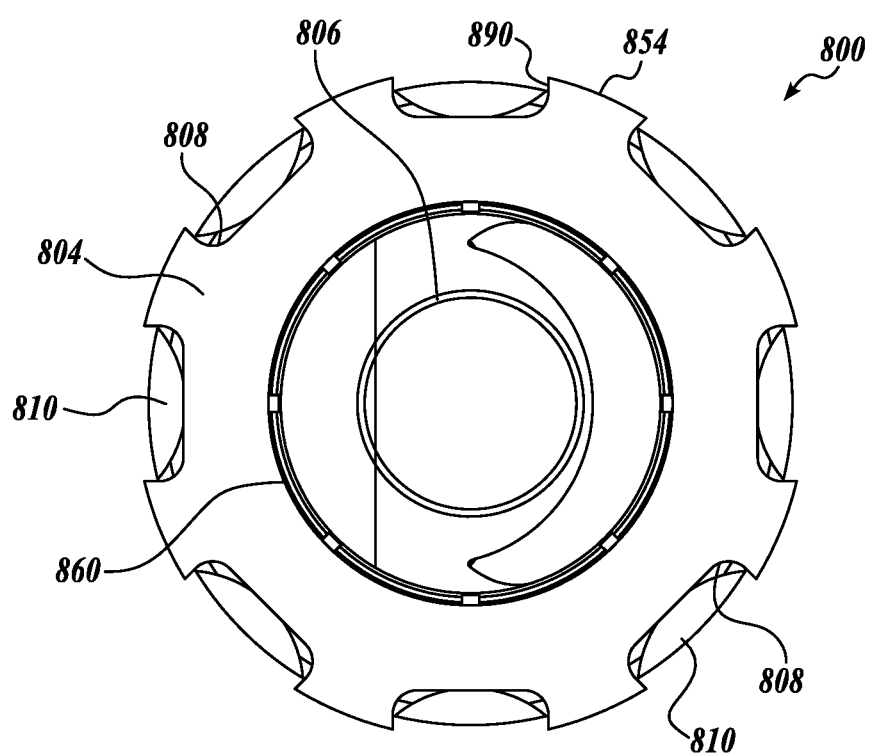

For example, in some embodiments, the tactile features 808 can be square or rectangular shaped channels but with small rounded fillets at the intersections between the bottom wall and the side walls of the channel. In some embodiments, each side wall extends slightly inwardly (toward the radial centerline of the channel (e.g., indentation)) into the channel at its outer end (adjacent the intersection with outer surface 854) so as to form a slight overhang 890, as shown in FIG. 37. The overhang, in some embodiments, improves the grip and/or leverage between the rotating portion 804 and the fingertip, thereby providing more precise control to the user. In some embodiments, the side walls are parallel to each other. In some embodiments, the side walls are parallel to each other and form right angles with the bottom wall of the channel. Of course, in other embodiments, the tactile features 808 can be indentations or channels having other shapes.

While illustrative embodiments have been illustrated and described, it will be appreciated that various changes can be made therein without departing from the spirit and scope of the disclosure. For example, while embodiments of the present disclosure have sometimes been described with respect to a Gonio lens, embodiments of the present disclosure apply to any ophthalmic contact lens for which rotation of the lens contact end on the eye is necessary or desirable.

The embodiments of the invention in which an exclusive property or privilege is claimed are defined as follows:

1. A lens indexing assembly having a central axis, comprising:
    a holding portion configured to support a rotating portion, wherein the holding portion has an outer surface configured for holding and a bearing surface;
    a rotating portion configured for coupling with the holding portion and configured to rotate relative to the holding portion, wherein the rotating portion has a bearing surface for rotating relative to the bearing surface of the holding portion, the rotating portion having an interface for coupling thereto to an ophthalmic contact lens coaxial with the central axis;
    wherein the rotating portion includes a plurality of tactile features spaced apart on an outer surface and configured to provide tactile feedback corresponding to a plurality of angular positions of the ophthalmic contact lens relative to the holding portion as the rotating portion rotates with respect to the holding portion, wherein a resistance to rotation of the rotating portion is provided solely by frictional contact between the holding portion and the rotating portion, said resistance to rotation being substantially constant during rotation of the rotating portion through all of the plurality of angular positions of the ophthalmic contact lens.

2. The assembly of claim 1, further comprising an ophthalmic contact lens configured for coupling with the rotating portion.

3. The assembly of claim 2, wherein the ophthalmic contact lens comprises at least one mirror placed at an angle relative to the optical axis of the eye.

4. The assembly of claim 1, wherein one of the outer surface of the holding portion or the bearing surface has a plurality of segments with recesses between segments; wherein the segments are depressible to coupled and decouple the rotating portion and the holding portion.

5. The assembly of claim 1, wherein the plurality of tactile features on the outer surface of the rotating portion are indentations on a surface of the rotating portion.

6. The assembly of claim 5, wherein the plurality of tactile features on the outer surface of the rotating portion are configured to receive a user's fingertip.

7. The assembly of claim 6, wherein each indentation has a U-shape.

8. The assembly of claim 1, wherein the holding portion includes at least one tactile feature on the outer surface of the holding portion, wherein each one of the plurality of tactile features on the outer surface of the rotating portion is configured to be alignable with the at least one tactile feature on the outer surface of the holding portion.

9. The assembly of claim 8, wherein the at least one tactile feature on the outer surface of the holding portion is configured to align with the plurality of tactile features on the outer surface of the rotating portion to provide said tactile feedback corresponding to a plurality of angular positions of the ophthalmic contact lens.

10. The assembly of claim 8, wherein each angular position corresponds to an indexing position of the ophthalmic contact lens.

11. The assembly of claim 8, wherein the holding portion includes a plurality of tactile features spaced apart on the outer surface of the holding portion.

12. The assembly of claim 1, wherein the plurality of tactile features on the outer surface of the rotating portion are U-shaped channels, each U-shaped channel having at least two outer edges used for rotating the rotating portion with respect to the holding portion, each U-shaped channel having side walls that are substantially parallel to each other and oriented orthogonally to a bottom wall of the U-shaped channel.

13. A lens indexing assembly having a central axis, the assembly comprising:
  a holding portion configured to support a rotating portion, wherein the holding portion has an outer surface configured for holding and a bearing surface, the holding portion including a at least one tactile feature on the outer surface;
  a rotating portion configured for coupling with the holding portion and configured to rotate relative to the holding portion, wherein the rotating portion has a bearing surface for rotating relative to the bearing surface of the holding portion, the rotating portion having an interface for coupling thereto an ophthalmic contact lens coaxial with the central axis;
  wherein the rotating portion includes a plurality of tactile features spaced apart on an outer surface, wherein the at least one tactile feature of the holding member is configured to align with each of the plurality of tactile features of the rotating portion as the rotating portion rotates with respect to the holding portion to provide tactile feedback corresponding to a plurality of angular positions of the ophthalmic contact lens relative to the holding portion,
  wherein a resistance to rotation of the rotating portion is provided solely by frictional contact between the holding portion and the rotating portion, said resistance to rotation being substantially constant during rotation of the rotating portion through all of the plurality of angular positions of the ophthalmic contact lens.

14. A lens indexing assembly having a central axis, the assembly comprising:
  a contact lens;
  a holding portion configured to support a rotating portion, wherein the holding portion has an outer surface configured for holding and a bearing surface, the holding portion including a plurality of tactile feature on the outer surface selected from the group consisting of protrusions and indentations;
  a rotating portion configured for coupling with the holding portion and configured to rotate relative to the holding portion about the central axis, wherein the rotating portion has a bearing surface for rotating relative to the bearing surface of the holding portion and an outer surface, the rotating portion including a plurality of tactile features on the outer surface selected from the group consisting of protrusions and indentations and a coupling interface coupled to the contact lens such that the contact lens is coaxial with the central axis, wherein the rotating portion is configured to rotate with respect to the holding portion between a plurality of indexing positions, each of the plurality of indexing positions corresponding to an angular position of the contact lens relative to the holding portion,
  wherein the plurality of tactile features of the rotating portion align with the plurality of tactile features of the holding portion to provide tactile feedback at each of the plurality of indexing positions as the rotating portion rotates with respect to the holding portion.

15. The assembly of claim 14, wherein a resistance to rotation of the rotating portion is provided by frictional contact between the holding portion and the rotating portion, the resistance to rotation being substantially constant through all of the plurality of indexing positions.

* * * * *